(12) United States Patent
Cockcroft et al.

(10) Patent No.: US 10,085,986 B2
(45) Date of Patent: Oct. 2, 2018

(54) PYRIMIDINONE COMPOUNDS AND THEIR USE

(75) Inventors: Xiao-Ling Fan Cockcroft, Horsham (GB); William Farnaby, Cambridge (GB); Natasha Kinsella, Kampala (UG); Kevin Merchant, Cambridge (GB); David Miller, Cambridge (GB)

(73) Assignee: Takeda Pharmaceutical Company Limited, Osaka (JP)

(*) Notice: Subject to any disclaimer, the term of this patent is extended or adjusted under 35 U.S.C. 154(b) by 293 days.

(21) Appl. No.: 14/131,337

(22) PCT Filed: Jul. 5, 2012

(86) PCT No.: PCT/GB2012/000573
§ 371 (c)(1),
(2), (4) Date: Apr. 11, 2014

(87) PCT Pub. No.: WO2013/004995
PCT Pub. Date: Jan. 10, 2013

(65) Prior Publication Data
US 2014/0248378 A1  Sep. 4, 2014

(30) Foreign Application Priority Data
Jul. 7, 2011 (GB) .................................. 1111705.8

(51) Int. Cl.
| C07F 9/02 | (2006.01) |
| A61K 31/513 | (2006.01) |
| C07D 239/54 | (2006.01) |
| C07D 239/60 | (2006.01) |
| A61K 45/06 | (2006.01) |
| C07D 239/22 | (2006.01) |
| C07D 401/12 | (2006.01) |
| C07D 403/12 | (2006.01) |
| C07D 405/12 | (2006.01) |
| C07D 413/12 | (2006.01) |
| C07D 471/04 | (2006.01) |

(52) U.S. Cl.
CPC ............ *A61K 31/513* (2013.01); *A61K 45/06* (2013.01); *C07D 239/22* (2013.01); *C07D 239/54* (2013.01); *C07D 239/60* (2013.01); *C07D 401/12* (2013.01); *C07D 403/12* (2013.01); *C07D 405/12* (2013.01); *C07D 413/12* (2013.01); *C07D 471/04* (2013.01)

(58) Field of Classification Search
CPC .... A61K 31/513; A61K 45/06; C07D 239/22; C07D 239/54; C07D 239/60; C07D 401/12; C07D 403/12; C07D 405/12; C07D 413/12; C07D 471/04
See application file for complete search history.

(56) References Cited

U.S. PATENT DOCUMENTS

| 4,193,916 A | 3/1980 | Back et al. |
| 4,694,008 A * | 9/1987 | Brown ................. C07D 239/52 |
| | | 514/269 |
| 4,743,685 A | 5/1988 | Breuer et al. |
| 5,244,890 A | 9/1993 | Yamanaka et al. |
| 5,401,734 A | 3/1995 | Yamanaka et al. |
| 5,532,354 A | 7/1996 | Yamanaka et al. |
| 5,962,480 A | 10/1999 | Moriguchi et al. |
| 9,180,122 B2 | 11/2015 | Farnaby et al. |
| 9,212,147 B2 | 12/2015 | Hondo et al. |
| 2010/0022526 A1 | 1/2010 | Lamberth et al. |
| 2013/0052281 A1 | 2/2013 | Farnaby et al. |
| 2014/0243353 A1 | 8/2014 | Farnaby et al. |
| 2014/0336165 A1 | 11/2014 | Hondo et al. |
| 2015/0030704 A1 | 1/2015 | Farnaby et al. |
| 2015/0329495 A1 | 11/2015 | Farnaby et al. |

FOREIGN PATENT DOCUMENTS

| BE | 859 477 | 4/1978 |
| DE | 2745024 | 10/1977 |
| EP | 0 180 298 A2 | 5/1986 |
| EP | 0 593 110 | 4/1994 |
| EP | 2 314 586 A1 | 4/2011 |

(Continued)

OTHER PUBLICATIONS

Division of Medicinal Chemistry Scientific Abstracts for the 244th National Meeting and Exposition, Aug. 19-23, 2012, Philadelphia, PA; publication date Jul. 6, 2012 (see Entry MEDI 98).
Dyumaev, K. M. et al., Aminometnylation of 2,3-dihydroxy- and 3-hydroxy-2-methoxypyridine. Zh., Khim, 1972, Abstr. No. 1Zh309, CAS Database Accession No. 1972:564402 CAPLUS.
English Abstract for BE859 477.
Hondo, et al., "4-Hydroxypyridazin-3(2H)-one derivatives as novel D-Amino acid oxidase inhibitors," J. Med. Chem. May 9, 2013; 56(9); 3582-92 (web publication date Apr. 8, 2013).
International Search Report and Written Opinion, PCT/GB2012/000672, dated Oct. 1, 2012.
International Search Report, PCT/GB2012/000574, dated Oct. 11, 2012.
Nakamura et al., "Studies on Prototropic Tautomerism in Nitrogen Heterocyclic Compounds, I. The Mannich Reaction of 2(1H)-Pyridone and 3-Hydroxy-2(1H)-pyridone)," Chem. Pharm. Bull., vol. 16, No. 8, 1966, 1466-1471.

(Continued)

*Primary Examiner* — David Browe
(74) *Attorney, Agent, or Firm* — Finnegan, Henderson, Farabow, Garrett & Dunner, LLP

(57) ABSTRACT

The present invention provides compounds of formula (1) and pharmaceutically acceptable salts thereof, wherein $R_1$, $R_2$, Y and Z are as defined in the specification, processes for their preparation, pharmaceutical compositions containing them and their use in therapy.

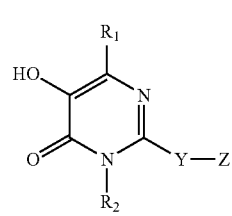

(1)

12 Claims, No Drawings

(56) References Cited

FOREIGN PATENT DOCUMENTS

| | | |
|---|---|---|
| GB | 2 025 416 | 1/1980 |
| JP | S61-057563 A | 3/1986 |
| JP | 62-84082 | 4/1987 |
| JP | S64-29367 A | 1/1989 |
| JP | H01-261392 A | 10/1989 |
| JP | 2002-028187 | 1/1990 |
| JP | H02-202875 A | 8/1990 |
| JP | H05-255344 A | 10/1993 |
| JP | 2009-02534 | 1/1997 |
| JP | 2001-519416 A | 10/2001 |
| JP | 2007-517056 | 6/2007 |
| WO | WO 9511235 A1 * | 4/1995 ........... C07D 239/36 |
| WO | WO 2002/053543 | 7/2002 |
| WO | WO 2003/062233 | 7/2003 |
| WO | WO2004/094408 A1 | 11/2004 |
| WO | WO2004094408 * | 11/2004 ........... C07D 403/04 |
| WO | WO 2005/061458 | 7/2005 |
| WO | WO 2005/066135 | 7/2005 |
| WO | WO 2006/135826 | 12/2006 |
| WO | WO2008/089453 A2 | 7/2008 |
| WO | WO 2008/115381 | 9/2008 |
| WO | WO 2008/116301 | 10/2008 |
| WO | WO2008/156607 A1 | 12/2008 |
| WO | WO 2009/020814 | 2/2009 |
| WO | WO 2010/017418 | 2/2010 |
| WO | WO 2011/046920 | 4/2011 |
| WO | WO 2011/109254 | 9/2011 |
| WO | WO 2011/109261 | 9/2011 |
| WO | WO2011/109267 A1 | 9/2011 |
| WO | WO 2013/003383 A1 | 1/2013 |
| WO | WO 2013/004996 | 1/2013 |
| WO | WO 2013/027000 | 2/2013 |
| WO | WO 2013/073577 | 5/2013 |
| WO | WO 2014/096757 | 6/2014 |

OTHER PUBLICATIONS

Nakamura et al., "Studies on Prototropic Tautomerism in Nitrogen Heterocyclic Compounds, II. A Ring-Chain Tautomerism in 3-Hydroxy-6-(2-oxocycloalkyl)-methyl-2(1H)-pyridone and 3-Hydroxy-6-(3-oxoalkyl)-2(1H)-pyridone Derivatives," Chem. Pharm. Bull., vol. 17, No. 3, 1969, 425-433.

Office Action (Restriction Requirement) dated Jan. 24, 2013, in U.S. Appl. No. 13/591,859.

Office Action dated Sep. 19, 2013, in U.S. Appl. No. 13/591,859.

U.S. Appl. No. 14/240,045, filed Feb. 21, 2014.

International Search Report, PCT/GB2012/000573, dated Sep. 10, 2012.

U.S. Appl. No. 14/358,162, filed May 14, 2014.

Hackam, et al., "Translation of Research Evidence from Animals to Humans," J. American Medical Association, 296(14), 2006, pp. 1731-1732.

Notice of Allowance dated Jul. 9, 2015, in U.S. Appl. No. 14/131,343.

Notice of Allowance dated Jul. 17, 2015, in U.S. Appl. No. 14/358,162.

Corrected Notice of Allowance dated Aug. 19, 2015, in U.S. Appl. No. 14/358,162.

U.S. Appl. No. 14/652,484, filed Jun. 16, 2015.

International Search Report for International Patent Application No. PCT/GB2013/000552, dated Mar. 20, 2014.

U.S. Appl. No. 14/885,037, filed Oct. 16, 2015.

Jordan, V. C., "Tamoxifen: A most unlikely pioneering medicine," Nature Reviews: Drug Discovery, 2, 2003, 205-213.

Notice of Allowance dated Nov. 3, 2015, in U.S. Appl. No. 14/240,045.

Office Action dated Mar. 19, 2015, in U.S. Appl. No. 14/131,343.

Office Action dated Mar. 16, 2015 (Restriction Requirement), in U.S. Appl. No. 14/240,045.

Office Action dated Mar. 18, 2015, in U.S. Appl. No. 14/358,162.

Office Action dated May 8, 2015, in U.S. Appl. No. 13/591,859.

Office Action dated Jun. 12, 2015, in U.S. Appl. No. 14/240,045.

Sunagawa et al., "Synthesis and Antibacterial Activity of Novel Carbapenems with a Catechol or Hydroxypyridone moiety," Journal of Antibiotics (1994), 47(11), 1354-1358.

Bluth, R., "Pharmacological Characterization of Novel Pyridazines," Pharmazie, vol. 36 No. 11, pp. 775-777 (1981).

Feng, Yucheng et al., "Photoclytic and Microbial Degradation of 3,5,6-trichioro-2-pyridinol," Environmental Toxicology and Chemistry, vol. 17, No. 5, pp. 814-819 (1998).

International Search Report for International Patent Application No. PCT/JP2012/079521, dated Jan. 22, 2013.

English Language Abstract of JP 02-028187.

English Language Abstract of JP 09-025234.

English Language Abstract of JP 62-84082.

English Language Abstract of JP 2007-517056.

Adage T., et al., "In vitro and in vivo pharmacological profile of AS057278, a selective D-amino acid oxidase inhibitor with potential anti-psychotic properties," European Neuropsychopharmacology 2008, 18, pp. 200-214.

Sparey T., et al., "The discovery of fused pyrrole carboxylic acids as novel, potent D-amino acid oxidase (DAO) inhibitors," Bioorganic & Medicinal Chemistry Letters, 2008, 18, pp. 3386-3391.

Ferraris D., et al., "Synthesis and Biological Evaluation of D-Amino Acid Oxidase Inhibitors," J. Med. Chem., 2008. 51, pp. 3357-3359.

Aroyan A., et al., Armyanskii Khimicheskii Zhurnal, vol. 27, No. 11, 1974, pp. 963-968.

Duplantier A., et al., "Discovery, SAR, and Pharmacokinetics of a Novel-3-Hydroxyquinolin-2(1H)-one Series of Potent D-Amino Acid Oxidase (DAAO) inhibitors," J. Med. Chem., 2009, 52, pp. 3576-3585.

U.S. Appl. No. 14/131,343.

U.S. Appl. No. 13/591,859.

Office Action issued in Japanese Patent Application No. 517912/2014 dated Feb. 24, 2016, 10 pages.

Vree, T.B., et al., "Novel Oxidative Pathways of Sulphapyridine and Sulphadiazine by the Turtle *Pseudemys Scripta Elegans,*" *The Veterniary Quarterly*, vol. 13, No. 4, Oct. 1991, downloaded by Japan Patent Office at 18:30 Feb. 9, 2016, pp. 218-224.

* cited by examiner

PYRIMIDINONE COMPOUNDS AND THEIR USE

This application is a national stage filing under 35 U.S.C. § 371 of International Application No. PCT/GB2012/000573 filed on 5 Jul. 2012, which claims priority of Great Britain Patent Application No. 1111705.1, filed on 7 Jul. 2011. The contents of both applications are incorporated herein by reference.

The present invention relates to pyrimidinone derivatives, processes for their preparation, pharmaceutical compositions containing them and their use in therapy, particularly in the treatment or prevention of conditions having an association with the D-amino acid oxidase enzyme (DAAO).

The hyper-dopaminergic theory has driven schizophrenia drug discovery for decades and has produced notable drugs such as clozapine and olanzapine. Although these medicaments can be highly efficacious against the positive symptoms of schizophrenia and have significantly benefited many patients they are not the complete answer, with fewer or no effects against the negative and cognitive aspects of the disease and with undesired side effect profiles in some cases. Amongst alternative hypotheses the hyper-glutamatergic theory has much merit with the first real evidence coming from the use of PCP (phencyclidine), MK801 or ketamine, direct N-methyl-D-aspartate (NMDA)-receptor antagonists that are able to produce schizophrenia-like symptomatology in healthy human volunteers or exacerbate the clinical signs in schizophrenia patients. However, direct modulation of the NMDA receptor using agonists has not proved successful with excitotoxicity (excessive stimulation by the neurotransmitter) leading to undesirable side effects. An alternative approach is to target the co-agonists required for NMDA receptor activation. These are glycine and serine (D-SER). Attempts to enhance NMDA receptor activity through the use of glycine transporter inhibitors have produced clinical compounds (but no marketed drugs to-date). D-SER is a co-agonist with even greater potency than glycine and so modulation of D-SER may represent an alternative strategy. One way to increase levels of D-SER is to reduce the activity of DAAO, the enzyme which removes it from the synaptic cleft.

DAAO enzyme inhibitors are known in the art. For example, Adage et al., *European Neuropsychopharmacology* 2008, 18, 200-214 have described AS-057278, a small molecule DAAO enzyme inhibitor. Likewise, Sparey et al., *Bioorganic & Medicinal Chemistry Letters*, 2008, 18, 3386-3391 have demonstrated that molecules containing small heterocyclic rings furnished with a carboxylic acid group can inhibit the DAAO enzyme. DAAO inhibitors which avoid the carboxylic acid group have been described by Ferraris et al., *J. Med. Chem.* 2008, 51, 3357-3359 and by Duplantier et al., *J. Med. Chem.* 2009, 52, 3576-3585. A further series of carboxylic acid-containing DAAO enzyme inhibitors from Sepracor are described in WO 2008089453.

European patent application EP0180298 discloses a class of pyrimidinone derivatives as histamine $H_2$ antagonists.

We have now discovered a new class of compounds that are DAAO enzyme inhibitors which have desirable activity profiles. The compounds of this invention have beneficial potency, selectivity and/or pharmacokinetic properties.

In accordance with the first aspect of the present invention, there is provided a compound having the formula (1):

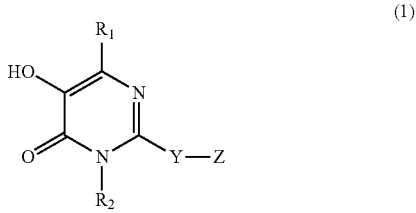

(1)

wherein:
$R_1$ represents H, halogen, $C_{1-6}$ alkyl, halo$C_{1-6}$alkyl or $C_{1-6}$ alkoxy;
$R_2$ represents H or $C_{1-6}$alkyl;
Y represents $^a$-$A_1$-S(O)$_p$-$A_2$-, $^a$-$A_1$-C(O)-$A_2$-, $^a A_3$-C(O)NR$_3$-$A_4$-, $^a A_3$-NR$_4$C(O)-$A_4$-, $^a A_3$-S(O)$_2$NR$_5$-$A_4$-, $^a A_3$-NR$_6$S(O)$_2$-$A_4$-, $^a$-$A_5$-O-$A_6$-, $C_{2-6}$ alkenylene, or $C_{2-6}$ alkylene optionally substituted with one or more $R_7$, each of which may be the same or different; $^a$ indicates the point of attachment to the pyrimidinyl ring;
p represents 0, 1 or 2;
$R_3$, $R_4$, $R_5$, $R_6$ independently represent H or $C_{1-6}$ alkyl;
$R_7$ represents $C_{1-6}$ alkyl or a $C_{1-6}$ alkylene chain attached to any other available carbon atom in the $C_{2-6}$ alkylene to which $R_7$ is attached to form a fused or spiro-fused $C_{3-6}$ cycloalkyl ring;
$A_1$ and $A_2$ each represent a covalent bond or $C_{1-3}$ alkylene optionally substituted with one or more $R_8$, each of which may be the same or different; wherein at least one of $A_1$ or $A_2$ is optionally substituted $C_{1-3}$ alkylene;
$A_3$ and $A_4$ each represent a covalent bond or $C_{1-3}$ alkylene optionally substituted with one or more $R_8$, each of which may be the same or different;
$A_5$ represents a covalent bond or $C_{1-2}$ alkylene optionally substituted with one or more $R_8$; $A_6$ represents a covalent bond or $C_{1-3}$ alkylene optionally substituted with one or more $R_8$ each of which may be the same or different; wherein at least one of $A_5$ or $A_6$ is optionally substituted alkylene;
$R_9$ represents $C_{1-6}$ alkyl;
Z represents aryl, heteroaryl, $C_{3-8}$ cycloalkyl or heterocyclyl; each of which may be optionally substituted with one or more $R_{10}$; wherein each $R_{10}$ may be the same or different;
$R_{10}$ represents -halogen, —$C_{1-6}$ alkyl, -halo$C_{1-6}$ alkyl, —$C_{0-6}$alkylCN, —$NO_2$, —$C_{0-6}$ alkyl-$CO_2R_{11}$, —$C_{0-6}$ alkyl-COR$_{11}$, —$C_{0-6}$ alkyl-NR$_{11}$R$_{14}$, —$C_{0-6}$ alkyl-CONR$_{11}$R$_{12}$, —$C_{0-6}$ alkyl-NR$_{11}$COR$_{12}$, —$C_{0-6}$ alkyl-N$_{11}$SO$_2$R$_{12}$, —$C_{0-6}$ alkyl-SO$_2$NR$_{11}$R$_{12}$, —$C_{0-6}$ alkyl-OCONR$_{11}$R$_{12}$, —$C_{0-6}$ alkyl-NR$_{11}$CO$_2$R$_{12}$, —$C_{0-6}$ alkyl-NR$_{11}$CONR$_{11}$R$_{12}$, —$C_{0-6}$ alkyl-OR$_{13}$, —$C_{0-6}$ alkyl-SR$_{14}$, —$C_{0-6}$ alkyl-SOR$_{14}$, —$C_{0-6}$ alkyl-SO$_2$R$_{14}$, —$C_{0-6}$ alkyl-OSO$_2$R$_{14}$, —$C_{0-6}$ alkyl-C$_{3-6}$cycloalkyl, —$C_{0-6}$alkyl-aryl, —$C_{0-6}$alkyl-heteroaryl, —$C_{0-6}$ alkyl-heterocyclyl, wherein said $C_{1-6}$ alkyl, —$C_{0-6}$ alkyl-$C_{3-6}$ cycloalkyl, —$C_{0-6}$alkyl-aryl, —$C_{0-6}$alkyl-heteroaryl, —$C_{0-6}$ alkyl-heterocyclyl is optionally substituted with one or more $R_{15}$, wherein each $R_{15}$ may be the same or different;
$R_{11}$ and $R_{12}$ independently represent H or $C_{1-6}$alkyl;
$R_{13}$ represents H, $C_{1-6}$alkyl, $C_{3-6}$ cycloalkyl, —$C_{1-6}$ alkyl-OR$_{18}$ or halo$C_{1-6}$ alkyl;
$R_{14}$ represents $C_{1-6}$alkyl;
$R_{15}$ represents halogen, $C_{1-6}$ alkyl, halo$C_{1-6}$ alkyl, —$C_{0-6}$ alkylCN, —$NO_2$, =O, —$C_{0-6}$ alkyl-CO$_2$R$_{16}$, —$C_{0-6}$ alkyl-COR$_{16}$, —$C_{0-6}$ alkyl-NR$_{16}$R$_{17}$, —$C_{0-6}$ alkyl-CONR$_{16}$R$_{17}$, —$C_{0-6}$ alkyl-NR$_{16}$COR$_{17}$, —$C_{0-6}$ alkyl-NR$_{16}$SO$_2$R$_{12}$, —$C_{0-6}$ alkyl-SO$_2$NR$_{16}$R$_{12}$, —$C_{0-6}$ alkyl-OCONR$_{16}$R$_{17}$, —$C_{0-6}$ alkyl-NR$_{16}$CO$_2$R$_{17}$, —$C_{0-6}$ alkyl-NR$_{16}$CONR$_{16}$R$_{12}$, —C$_{0-6}$ alkyl-OR$_{18}$, —C$_{0-6}$ alkyl-SR$_{19}$, —C$_{0-6}$ alkyl-SOR$_{19}$, —C$_{0-6}$ alkyl-SO$_2$R$_{19}$ or —C$_{0-6}$ alkyl-OSO$_2$R$_{19}$;

R$_{16}$ and R$_{17}$ independently represent H or C$_{1-6}$alkyl;
R$_{18}$ represents H, C$_{1-6}$alkyl or -haloC$_{1-6}$ alkyl; and
R$_{19}$ represents C$_{1-6}$alkyl;

or a pharmaceutically acceptable salt thereof.

Where any group in the compound of formula (1) above is referred to as being optionally substituted, this group may be unsubstituted or substituted by one or more substituents. Typically any such group will be unsubstituted, or substituted by one, two or three substituents.

In the compounds of the invention as represented by formula (1) and the more detailed description hereinafter certain of the general terms used in relation to substituents are to be understood to include the following atoms or groups unless otherwise specified.

The term 'halogen' as used herein refers to a fluorine, chlorine, bromine or iodine atom, unless otherwise specified, typically fluorine or chlorine.

The term 'hydroxyl' as used herein refers to OH.

The term 'C$_{x-y}$ alkyl' as used herein refers to a linear or branched saturated hydrocarbon group containing from x to y carbon atoms. For example, C$_{1-6}$ alkyl refers to a linear or branched saturated hydrocarbon group containing from 1 to 6 carbon atoms. Examples of C$_{1-6}$ alkyl groups include methyl, ethyl, n-propyl, isopropyl, n-butyl, isobutyl, sec-butyl, tert butyl, n-pentyl, isopentyl, neopentyl and hexyl. C$_0$alkyl indicates that the group is absent i.e. there is a direct bond between the groups.

For the avoidance of doubt, when any one of A$_1$ to A$_6$ represents an alkylene chain substituted by an alkyl substituent R$_3$, then the alkyl substituent R$_8$ is attached off the alkylene chain and is not attached so that it extends the alkylene chain. For example, if A$_1$ represents a C$_2$ alkylene substituted by methyl, then A$_1$ would have one of the following structures:

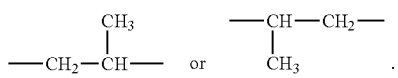

The term 'C$_{x-y}$alkoxy' as used herein refers to an —O—C$_{x-y}$ alkyl group wherein C$_{x-y}$ alkyl is as defined herein. Examples of C$_{1-6}$alkoxy groups include methoxy, ethoxy, propoxy, butoxy, pentoxy and hexoxy.

The term 'haloC$_{x-y}$alkyl' as used herein refers to a C$_{x-y}$ alkyl group as defined herein wherein at least one hydrogen atom is replaced with halogen. Examples of such groups include fluoroethyl, trifluoromethyl and trifluoroethyl.

The term 'C$_{1-3}$ hydroxyalkyl' as used herein refers to a C$_{1-3}$alkyl group as defined herein wherein at least one hydrogen atom is replaced with hydroxyl. Examples of C$_{1-3}$ hydroxyalkyl groups include hydroxymethyl and hydroxyethyl.

The term 'C$_{1-6}$ alkylene' as used herein refers to a divalent hydrocarbon group obtained by removing one hydrogen atom from 'C$_{1-6}$ alkyl' above. Examples of C$_{1-3}$alkylene groups include methylene, methylmethylene, dimethylmethylene, ethylene and propylene.

The term 'C$_{x-y}$ alkenylene' as used herein refers to a divalent hydrocarbon group obtained by removing one hydrogen atom from 'C$_{x-y}$ alkenyl', in which 'C$_{x-y}$ alkenyl' refers to a linear or branched hydrocarbon group containing one or more carbon-carbon double bonds and having from x to y carbon atoms. Examples of C$_{2-6}$ alkenylene groups include vinylene and propenylene.

The term 'C$_{x-y}$ cycloalkyl' as used herein refers to a saturated monocyclic hydrocarbon ring of x to y carbon atoms. For example, C$_{3-8}$ cycloalkyl refers to a saturated monocyclic hydrocarbon ring of 3 to 8 carbon atoms. Examples of C$_{3-8}$ cycloalkyl groups include cyclopropyl, cyclobutyl, cyclopentyl, cyclohexyl and cycloheptyl.

The term 'aryl' as used herein refers to a C$_{6-12}$ monocyclic or bicyclic hydrocarbon ring wherein at least one ring is aromatic. Examples of monocyclic ring systems include phenyl. Examples of bicyclic ring systems in which both rings are aromatic include naphthalenyl. The term 'aryl' is also intended to refer to bicyclic ring systems wherein a monocyclic aromatic ring system e.g. phenyl is fused to a non-aromatic ring system e.g. C$_{3-8}$ cycloalkyl or 4-7 membered monocyclic heterocyclyl ring, as defined herein. Examples of such groups include tetrahydronaphthalenyl, 2,3-dihydro-1,4,-benzodioxin-5-yl and 2,3-dihydro-1-benzofuran-5-yl.

It will be appreciated that the aryl group may be attached to the rest of the molecule through any available atom.

The term 'heteroaryl' as used herein refers to a 5-6 membered monocyclic aromatic or a fused 8-10 membered bicyclic aromatic ring which monocyclic or bicyclic ring contains 1 to 4 heteroatoms selected from oxygen, nitrogen and sulphur. Examples of such monocyclic aromatic rings include thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidinyl, pyridazinyl, pyrazinyl, pyridinyl, triazinyl, tetrazinyl and the like. Examples of such bicyclic aromatic rings include quinolinyl, isoquinolinyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridinyl, furopyridinyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl and imidazopyridinyl.

It will be appreciated that any heteroaryl ring may be attached to the rest of the molecule through any available C or N atom. Optional substituents may be present on any available C or N atom.

When the 'heteroaryl' contains a nitrogen atom as its ring-constituting atom, the nitrogen atom may be oxidized. For instance, pyridinyl as the 'heteroaryl' may be its N-oxide.

The term 'heterocyclyl' refers to a 4-7 membered monocyclic ring or an 8-12 membered bicyclic, bridged or spiro-fused ring, any of which may be saturated or partially unsaturated, which monocyclic or bicyclic ring contains 1 to 4 heteroatoms selected from oxygen, nitrogen, silicon or sulphur.

Examples of such monocyclic groups include pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridinyl, dihydropyridinyl, tetrahydropyrimidinyl, dihydropyrimidinyl, tetrahydropyridazinyl, dihydropyridazinyl, tetrahydropyrazinyl, dihydropyrazinyl, tetrahydrothiophenyl, tetrahydrothiopyranyl, diazepanyl, azepanyl and oxazepanyl. Examples of such 7-12 membered bicyclic, bridged or spiro-fused rings include indolinyl, isoindolinyl, benzopyranyl, quinuclidinyl, 2,3,4,5-tetrahydro-1H-3-benzazepine and tetrahydroisoquinolinyl 'Pharmaceutically acceptable salts' of compounds of formula (1) of the present invention include salts with inorganic bases, salts with organic bases, salts with inorganic acids, salts with organic acids and salts with basic or acidic amino acids. Salts with acids may, in particular, be employed in some instances. In particular, 'pharmaceutically acceptable salts' of compounds of formula (1) of the present invention include but are not limited to acid addition salts such as a hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-naphthoate (xinafoate), methanesulphonate or p-toluenesulphonate salt, and salts of amino acids (such as glycine, alanine, valine, leucine, isoleucine, cysteine, methionine, proline). Further pharmaceutically acceptable salts include quaternary ammonium salts of the compounds of formula (1).

Compounds of formula (1) and their salts may be in the form of a solvate, which is included in the scope of the invention. Such solvates may be formed with common organic solvents, including but not limited to, alcoholic solvents e.g. methanol, ethanol or isopropanol.

The compounds of formula (1) of the present invention may be in either hydrate or non-hydrate form.

Where compounds of the invention exist in different enantiomeric and/or diastereoisomeric forms (including geometric isomerism about a double bond), these compounds may be prepared as isomeric mixtures or racemates, although the invention relates to all such enantiomers or isomers, whether present in an optically pure form or as mixtures with other isomers. Individual enantiomers or isomers may be obtained by methods known in the art, such as optical resolution of products or intermediates (for example chiral chromatographic separation (e.g. chiral HPLC), or an enantiomeric synthesis approach. Similarly, where compounds of the invention may exist as alternative tautomeric forms (e.g. ketoenol, amideimidic acid), the invention relates to the individual tautomers in isolation, and to mixtures of the tautomers in all proportions. For example, compounds of formula (1) in which $R_2$ represents H, may exist as:

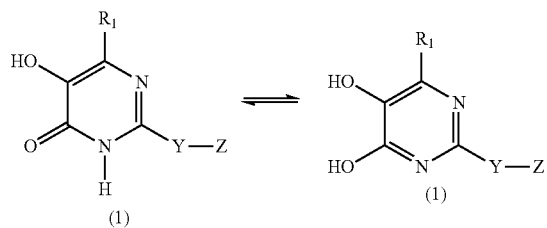

In one aspect of the invention, compounds of formula (1) may bear one or more radiolabels. Such radiolabels may be introduced by using radiolabel-containing reagents in the synthesis of the compounds of formula (1), or may be introduced by coupling the compounds of formula (1) to chelating moieties capable of binding to a radioactive metal atom. Such radiolabeled versions of the compounds may be used, for example, in diagnostic imaging studies.

In one embodiment, $R_1$ represents H or halo$C_{1-6}$ alkyl. $R_1$ typically represents H or trifluoromethyl.

In certain embodiments, $R_1$ represents a hydrogen atom.

In one embodiment, $R_2$ represents H or $C_{1-3}$ alkyl, typically methyl. In certain embodiments, $R_2$ represents a hydrogen atom.

$A_1$, $A_2$, $A_3$, $A_4$, $A_5$ and $A_6$ typically represent a covalent bond or methylene or ethylene optionally substituted with one or more $R_8$. $R_8$ typically represents methyl.

Specific examples for $A_1$, $A_2$, $A_3$, $A_4$, $A_5$ and $A_6$ include a covalent bond, —CH$_2$—, —CH$_2$CH$_2$—, —CH(CH$_3$)— or —C(CH$_3$)$_2$—. Typically $A_1$, $A_2$, $A_3$, $A_4$, $A_5$ and $A_6$ represent a covalent bond or —CH$_2$—.

Suitable examples of spiro-fused or fused $C_{3-6}$ cycloalkyl rings formed when Y represents $C_{2-6}$ alkylene substituted with a $C_{1-6}$ alkylene chain attached to any other available carbon atom in the $C_{2-6}$ alkylene to which it is attached include:

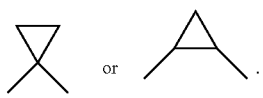

Specific examples of Y include —CH$_2$—S—, —CH$_2$—S(O)$_2$—, —CH(CH$_3$)—S—, —CH(CH$_3$)—S(O)$_2$—, —S—CH$_2$—, —S(O)$_2$—CH$_2$, —S(O)$_2$—CH(CH$_3$)—, —CH$_2$—C(O)—, —CH(CH$_3$)—C(O)—, —C(O)—CH$_2$—, —C(O)—CH(CH$_3$)—, —C(O)NR$_3$—, —CH$_2$—C(O)NR$_3$—, —CH(CH$_3$)—C(O)NR$_3$—, —C(O)NR$_3$—CH$_2$—, —C(O)NR$_3$—CH(CH$_3$)—, —NR$_4$C(O)—, —CH$_2$—NR$_4$C(O)—, —CH(CH$_3$)—NR$_4$C(O)—, —NR$_4$C(O)—CH$_2$—, —NR$_4$C(O)—CH(CH$_3$)—, —S(O)$_2$NR$_5$—, —CH$_2$—S(O)$_2$NR$_5$—, —CH(CH$_3$)—S(O)$_2$NR$_5$—, —S(O)$_2$NR$_5$—CH$_2$—, —S(O)$_2$NR$_5$—CH(CH$_3$)—, —NR$_6$S(O)$_2$—, —CH$_2$—NR$_6$S(O)$_2$—, —CH(CH$_3$)—NR$_6$S(O)$_2$—, —NR$_6$S(O)$_2$—CH$_2$—, —NR$_6$S(O)$_2$—CH(CH$_3$)—, —CH$_2$—O—, —CH(CH$_3$)—O—, —O—CH$_2$—, —O—CH(CH$_3$)—, —CH$_2$—CH$_2$—, —CH$_2$—CH(CH$_3$)—, —CH$_2$—C(CH$_3$)$_2$—, —C(CH$_3$)$_2$—CH$_2$—,

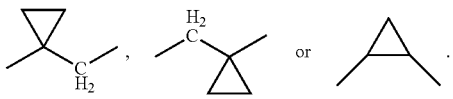

In one embodiment, Y represents $^a$-A$_1$-S(O)$_p$-A$_2$-, $^a$-A$_5$-O-A$_6$-, or $C_{2-6}$ alkylene optionally substituted with one or more $R_7$. Typically, p represents 0.

In a further embodiment, Y represents $^a$—C$_{1-3}$alkylene-O—, $^a$—C$_{1-3}$alkylene-S—, $^a$—S—C$_{1-3}$ alkylene-, in which the C$_{1-3}$alkylene is optionally substituted as defined herein; or $C_{2-6}$ alkylene optionally substituted with one or more $R_7$. $R_7$ typically represents $C_{1-6}$ alkyl.

Representative examples of Y include, $^a$—CH$_2$—O—, $^a$—CH$_2$—S—, $^a$—S—CH$_2$—, $^a$—S—CH(CH$_3$)—, and —CH$_2$CH$_2$—.

In one particular embodiment, Y represents $^a$—S—C$_{1-3}$ alkylene-. In a further embodiment, Y represents $^a$—S—CH$_2$— or $^a$—S—CH(CH$_3$)—. In yet a further embodiment, Y represents $^a$—S—CH$_2$—.

In one aspect of the invention, Y may represent $^a$-A$_1$-S(O)$_p$-A$_2$-, $^a$-A$_1$-C(O)-A$_2$-, $^a$A$_3$-C(O)NR$_3$-A$_4$, $^a$A$_3$-NR$_4$C(O)-A$_4$-, $^a$A$_3$-S(O)$_2$NR$_5$-A$_4$, $^a$A$_3$-NR$_6$S(O)$_2$-A$_4$, $^a$-A$_5$-O-A$_6$- or $C_{2-6}$ alkenylene.

In another aspect, Y may represent $^a$—S-A$_2$-, —S(O)-A$_2$-, —S(O)$_2$-A$_2$-, A$_1$-C(O)-A$_2$-, $^a$A$_3$-C(O)NR$_3$-A$_4$, $^a$A$_3$-NR$_4$C(O)-A$_4$-, $^a$A$_3$-S(O)$_2$NR$_5$-A$_4$, $^a$A$_3$-NR$_6$S(O)$_2$-A$_4$, A$_6$- or $C_{2-6}$ alkenylene.

In one embodiment Z represents aryl, heteroaryl or $C_{3-8}$ cycloalkyl, each of which may be optionally substituted with one or more $R_{10}$.

Typical examples of aryl, heteroaryl or $C_{3-8}$ cycloalkyl rings represented by Z include, phenyl, naphthalenyl, 2,3-dihydro-1,4,-benzodioxin-5-yl, 2,3-dihydro-1-benzofuran-5-yl, pyrazolyl, pyridinyl, isoquinolinyl, imidazopyridinyl and cyclopropyl, each of which may be optionally substituted with one or more $R_{10}$.

In a further embodiment, Z represents aryl or heteroaryl, each of which may be optionally substituted with one or more $R_{10}$. In one embodiment Z represents phenyl or pyridinyl, each of which may be optionally substituted with one or more $R_{10}$.

In yet a further embodiment, Z represents optionally substituted aryl, typically optionally substituted phenyl or naphthalenyl.

Z is typically unsubstituted or mono- or di-substituted. In one embodiment Z is unsubstituted. In another embodiment Z is monosubstituted. In another embodiment Z is disubstituted.

In one embodiment, $R_{10}$ represents -halogen, $—C_{1-6}$ alkyl, -halo$C_{1-6}$ alkyl, $—C_{0-6}$ alkyl-$OR_{13}$ or $—C_{0-6}$alkyl-heteroaryl, wherein said $C_{1-6}$ alkyl or $—C_{0-6}$alkyl-heteroaryl, is optionally substituted with one or more $R_{15}$, wherein each $R_{15}$ may be the same or different.

Suitable heteroaryl groups present when $R_{10}$ represents $—C_{0-6}$alkyl-heteroaryl include monocyclic heteroaryl groups, including thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidinyl, pyridazinyl, pyrazinyl, pyridinyl, triazinyl and tetrazinyl. Specific examples of $R_{10}$—$C_{0-6}$alkyl-heteroaryl include 5-methyl-1,2,4-oxadiazol-3-yl.

In a further embodiment, $R_{10}$ represents -halogen, $—C_{1-6}$ alkyl, -halo$C_{1-6}$ alkyl or $—OR_{13}$, wherein said $C_{1-6}$ alkyl is optionally substituted with one or more $R_{15}$, wherein each $R_{15}$ may be the same or different.

In one embodiment $R_{13}$ represents $C_{1-6}$alkyl or -halo$C_{1-6}$ alkyl.

Suitably $R_{13}$ represents methyl, difluoromethyl, trifluoromethyl or 2,2,2-trifluoroethyl.

In one embodiment, $R_{15}$ represents $—C_{1-6}$ alkyl. Typically $R_{15}$ represents methyl.

Representative examples of $R_{10}$ include, fluorine, chlorine, methyl, trifluoromethyl, methoxy, difluoromethoxy, trifluoromethoxy, 2,2,2-trifluoroethoxy and 5-methyl-1,2,4-oxadiazol-3-yl.

Specific examples of Z include, phenyl, 3-methylphenyl, 2-chlorophenyl, 3-chlorophenyl, 4-chlorophenyl, 3-fluorophenyl, 3,4-difluorophenyl, 3-methoxyphenyl, 4-methoxyphenyl, 3-trifluoromethylphenyl, 3-chloro-5-fluorophenyl, 3-difluoromethoxyphenyl, 2-(2,2,2-trifluoroethoxy)phenyl, 4-fluoro-3-(trifluoromethoxy)phenyl, 3-(5-methyl-1,2,4-oxadiazol-3-yl)phenyl, naphthalen-1-yl, naphthalen-2-yl, 2,3-dihydro-1,4-benzodioxin-5-yl, 2,3-dihydro-1-benzo furan-5-yl, pyridin-2-yl, pyridin-3-yl, pyridin-4-yl, 4-methylpyridin-2-yl, 1,3-dimethyl-1H-pyrazol-5-yl, isoquinolin-1-yl, imidazo[1,2-a]pyridin-6-yl, imidazo[1,2-a]pyridin-2-yl and cyclopropyl.

One sub-class of compounds according to the invention is represented by the compounds of formula (1A)

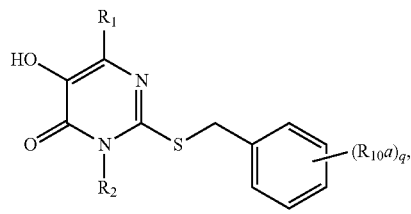

(1A)

wherein $R_1$ and $R_2$ are as herein defined; q represents 0, 1 or 2 and $R_{10}a$ is as defined for $R_{10}$;
or a pharmaceutically acceptable salt thereof.

In one embodiment $R_{10}a$ represents -halogen, $—C_{1-6}$ alkyl, -halo$C_{1-6}$alkyl, $—C_{0-6}$ alkyl-$OR_{13}$ or $—C_{0-6}$alkyl-heteroaryl, wherein said $C_{1-6}$ alkyl or $—C_{0-6}$alkyl-heteroaryl, is optionally substituted with one or more $R_{15}$, wherein each $R_{15}$ may be the same or different; where $R_{13}$ and $R_{15}$ are as herein defined.

In a further embodiment, $R_{10}a$ represents -halogen, $—C_{1-6}$ alkyl, -halo$C_{1-6}$ alkyl or $—OR_{13}$, wherein said $C_{1-6}$ alkyl is optionally substituted with one or more $R_{15}$, wherein each $R_{15}$ may be the same or different.

In yet a further embodiment, $R_{10}a$ represents fluoro, chloro, methyl, trifluoromethyl, methoxy, difluoromethoxy or trifluoromethoxy.

It will be appreciated that when q represents 2, each $R_{10a}$ may be the same or different.

In one embodiment, $R_{10}a$, when present, is attached to the phenyl ring via the 3-, 4- or -5 positions.

In a further aspect of the invention, specific novel compounds include each of the novel compounds whose preparation is described in the accompanying Examples, and pharmaceutically acceptable salts thereof.

In particular embodiments the compound of formula (1) is selected from the group consisting of:
2-(3-chlorobenzylthio)-5-hydroxypyrimidin-4(3H)-one;
2-(benzylsulfanyl)-5-hydroxypyrimidin-4(3H)-one;
5-hydroxy-2-[(3-methylbenzyl)sulfanyl]pyrimidin-4(3H)-one;
2[(4-chlorobenzyl)sulfanyl]-5-hydroxypyrimidin-4(3H)-one;
5-hydroxy-2-[(naphthalen-2-ylmethyl)sulfanyl]pyrimidin-4(3H)-one;
2-[(3-fluorobenzyl)sulfanyl]-5-hydroxypyrimidin-4(3H)-one;
5-hydroxy-2-[(4-methoxybenzyl)sulfanyl]pyrimidin-4(3H)-one;
2-[(3,4-difluorobenzyl)sulfanyl]-5-hydroxypyrimidin-4(3H)-one;
5-hydroxy-2-[(3-methoxybenzyl)sulfanyl]pyrimidin-4(3H)-one;
5-hydroxy-2-{[3-(trifluoromethyl)benzyl]sulfanyl}pyrimidin-4(3H)-one;
2-[(3-chloro-5-fluorobenzyl)sulfanyl]-5-hydroxypyrimidin-4(3H)-one;
5-hydroxy-2-{[3-(5-methyl-1,2,4-oxadiazol-3-yl)benzyl]sulfanyl}-pyrimidin-4(3H)-one;
2-[(2-chlorobenzyl)sulfanyl]-5-hydroxypyrimidin-4(3H)-one;
5-hydroxy-2-[(1-phenylethyl)sulfanyl]pyrimidin-4(3H)-one;
2-(cyclopropylmethylthio)-5-hydroxypyrimidin-4(3H)-one;
2-[(2,3-dihydro-1,4-benzodioxin-5-ylmethyl)sulfanyl]-5-hydroxypyrimidin-4(3H)-one;

5-hydroxy-2-(pyridin-2-ylmethylthio)pyrimidin-4(3H)-one;
2-(3-(difluoromethoxy)benzylthio)-5-hydroxypyrimidin-4 (3H)-one;
5-hydroxy-2-((4-methylpyridin-2-yl)methylthio)pyrimidin-4(3H)-one;
5-hydroxy-2-(pyridin-3-ylmethylthio)pyrimidin-4(3H)-one;
2((1,3-dimethyl-1H-pyrazol-5-yl)methylthio)-5-hydroxypyrimidin-4(3H)-one;
5-hydroxy-2-(pyridin-4-ylmethylthio)pyrimidin-4(3H)-one;
2-(4-fluoro-3-(trifluoromethoxy)benzylthio)-5-hydroxypyrimidin-4(3H)-one;
5-hydroxy-2-[(isoquinolin-1-ylmethyl)sulfanyl]pyrimidin-4 (3H)-one;
5-hydroxy-2-{[2-(2,2,2-trifluoroethoxy)benzyl]sulfanyl}-pyrimidin-4(3H)-one;
5-hydroxy-2-[(imidazo[1,2-a]pyridin-6-ylmethyl)sulfanyl]-pyrimidin-4(3H)-one;
2-[(2,3-dihydro-1-benzofuran-5-ylmethyl)sulfanyl]-5-hydroxypyrimidin-4(3H)-one;
5-hydroxy-2-[(naphthalen-1-ylmethyl)sulfanyl]pyrimidin-4 (3H)-one;
5-hydroxy-2-[(imidazo[1,2-a]pyridin-2-ylmethyl)sulfanyl]-pyrimidin-4(3H)-one;
5-hydroxy-2-[(phenylsulfanyl)methyl]pyrimidin-4(3H)-one;
5-hydroxy-2-(phenoxymethyl)pyrimidin-4(3H)-one;
2-[2-(3-chlorophenyl)ethyl]-5-hydroxypyrimidin-4(3H)-one;
5-hydroxy-2-(2-phenylethyl)pyrimidin-4(3H)-one;
2-(benzylsulfanyl)-5-hydroxy-6-(trifluoromethyl)pyrimidin-4(3H)-one;
5-methoxy-2-(4-methoxybenzylthio)pyrimidin-4(3H)-one;
and pharmaceutically acceptable salts thereof.

Particularly useful compounds in accordance with the invention include each of the compounds described in the accompanying examples, and pharmaceutically acceptable salts thereof.

The compounds of formula (1) and their pharmaceutically acceptable salts have activity as pharmaceuticals, in particular as D-amino acid oxidase enzyme (DAAO) inhibitors, and thus may be used in the treatment of schizophrenia and other psychotic disorders (e.g., psychotic disorder, psychosis), dementia and other cognitive disorders, anxiety disorders (e.g., generalized anxiety disorder), mood disorders (e.g., depressive disorders, major depressive disorders, bipolar disorders including bipolar I and II, bipolar mania, bipolar depression), sleep disorders, disorders usually first diagnosed in infancy, childhood, or adolescence (e.g., attention-deficit disorder and disruptive behaviour disorders), pain (e.g. neuropathic pain) and neurodegenerative disorders (e.g. Parkinson's or Alzheimer's disease).

Thus, the present invention provides a compound of formula (1) or a pharmaceutically acceptable salt thereof as hereinbefore defined for use in therapy, in particular for the treatment of conditions whose development or symptoms are linked to DAAO enzyme activity.

The present invention also provides the use of a compound of formula (1) or a pharmaceutically acceptable salt thereof as hereinbefore defined for the preparation of a medicament for the treatment of conditions whose development or symptoms are linked to DAAO enzyme activity.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

In particular, the compounds of the invention (including pharmaceutically acceptable salts) may be used in the treatment of the positive symptoms of schizophrenia, schizophreniform disorder or schizoaffective disorder (e.g. voices or hallucinations), cognitive disorders (such as dementia and impaired learning) and also pain (such as neuropathic pain).

The invention also provides a method of treating at least one symptom or condition associated with schizophrenia, schizophreniform disorder, schizoaffective disorder and other psychotic disorders (e.g., psychotic disorder, psychosis), dementia and other cognitive disorders, anxiety disorders (e.g., generalized anxiety disorder), mood disorders (e.g., depressive disorders, major depressive disorders, bipolar disorders including bipolar I and II, bipolar mania, bipolar depression), sleep disorders, disorders usually first diagnosed in infancy, childhood, or adolescence (e.g., attention-deficit disorder, autistic spectrum disorders and disruptive behaviour disorders), pain (e.g. neuropathic pain) and neurodegenerative disorders (e.g. Parkinson's or Alzheimer's disease) which comprises administering to a patient in need thereof a therapeutically effective amount of a compound of formula (1) or a pharmaceutically acceptable salt thereof as hereinbefore defined.

Such symptoms and conditions include, but are not limited to, anxiety, agitation, hostility, panic, an eating disorder, an affective symptom, a mood symptom, a negative and positive psychotic symptom commonly associated with psychosis and neurodegenerative disorder.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (µg/kg) to 100 micrograms per kilogram body weight (µg/kg). Alternatively, if the compound is administered orally, then the daily dosage of the compound of the invention may be in the range from 0.01 micrograms per kilogram body weight (µg/kg) to 100 milligrams per kilogram body weight (mg/kg).

The compounds of formula (1) and pharmaceutically acceptable salts thereof may be used on their own but will generally be administered in the form of a pharmaceutical composition in which the formula (1) compound/salt (active ingredient) is in association with a pharmaceutically acceptable adjuvant, diluent or carrier.

Therefore the present invention further provides a pharmaceutical composition comprising a compound of formula (1) or a pharmaceutically acceptable salt thereof as hereinbefore defined, in association with a pharmaceutically acceptable adjuvant, diluent or carrier.

The invention still further provides a process for the preparation of a pharmaceutical composition of the invention which comprises mixing a compound of formula (1) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant such as that described in Ph. Helv. or a similar alcohol.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of the invention (that is, compounds of formula (1) and pharmaceutically acceptable salts thereof) may also be administered in conjunction with other compounds used for the treatment of the above conditions.

The invention therefore further relates to combination therapies wherein a compound of the invention or a pharmaceutical composition or formulation comprising a compound of the invention is administered with another therapeutic agent or agents, for the treatment of one or more of the conditions previously indicated. Such therapeutic agents may be selected from the following:

(i) antidepressants such as, for example, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, thionisoxetine, tranylcypromaine, trazodone, trimipramine, venlafaxine, and equivalents and pharmaceutically active isomer(s) and/or metabolite(s) thereof;

(ii) atypical antipsychotics including, for example, quetiapine and pharmaceutically active isomer(s) and/or metabolite(s) thereof;

(iii) antipsychotics including, for example, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutlypiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone, and equivalents and pharmaceutically active isomer(s) and/or metabolite(s) thereof;

(iv) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reel azepam, tracazolate, trepipam, temazepam, triazolam, uldazepam, and zolazepam; and equivalents and pharmaceutically active isomer(s) and/or metabolite(s) thereof;
(v) anticonvulsants including, for example, carbamazepine, valproate, lamotrigine, and gabapentin, and equivalents and pharmaceutically active isomer(s) and/or metabolite(s) thereof;
(vi) Alzheimer's therapies including, for example, donepezil, memantine, tacrine, and equivalents and pharmaceutically active isomer(s) and/or metabolite(s) thereof;
(vii) Parkinson's therapies including, for example, deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;
(viii) migraine therapies including, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, and zomitriptan, and equivalents and pharmaceutically active isomer(s) and/or metabolite(s) thereof;
(ix) stroke therapies including, for example, abciximab, activase, NXY-059, citicoline, crobenetine, desmoteplase, repinotan, traxoprodil, and equivalents and pharmaceutically active isomer(s) and/or metabolite(s) thereof;
(x) urinary incontinence therapies including, for example, darafenacin, falvoxate, oxybutynin, propiverine, robalzotan, solifenacin, and tolterodine, and equivalents and pharmaceutically active isomer(s) and/or metabolite(s) thereof;
(xi) neuropathic pain therapies including, for example, gabapentin, lidoderm, and pregablin, and equivalents and pharmaceutically active isomer(s) and/or metabolite(s) thereof;
(xii) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;
(xiii) insomnia therapies including, for example, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos, secobarbital, zaleplon, and Zolpidem, and equivalents and pharmaceutically active isomer(s) and/or metabolite(s) thereof;
(xiv) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/or metabolite(s) thereof;
(xv) 5HT1B ligands such as, for example, compounds disclosed in WO 9905134 and WO 0208212;
(xvi) mGluR2 agonists;
(xvii) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947;
(xviii) chemokine receptor CCRI inhibitors; and
(xix) delta opioid agonists such as, for example, compounds disclosed in WO 97/23466 and WO 02/094794.

Such combination products employ the compounds of this invention within the dosage range described herein and the other pharmaceutically active agent within approved dosage ranges and/or the dosage such as described in the publication reference.

In a further aspect the present invention provides a combination (for example for the treatment of schizophrenia, cognitive disorders or pain) of a compound of formula (1) or a pharmaceutically acceptable salt thereof as hereinbefore defined and one or more agents selected from carbamazepine, olanzapine, quetiapine, verapamil, lamotrigine, oxcarbazepine, risperidone, aripiprazole, ziprasidone and lithium.

The invention also provides a pharmaceutical product comprising, in combination, a preparation of a first active ingredient which is a compound of formula (1) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, for simultaneous, sequential or separate use in therapy.

In another aspect, the invention provides a kit comprising a preparation of a first active ingredient which is a compound of formula (1) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, and instructions for the simultaneous, sequential or separate administration of the preparations to a patient in need thereof.

In the following process description, the symbols $R_1$, $R_2$, $R_3$, $R_4$, $R_5$, $R_6$, $R_7$, $R_8$, Y, Z, $A_1$, $A_2$, $A_3$, $A_4$, $A_5$ and $A_6$ when used in the formulae depicted are to be understood to represent those groups as described above in relation to formula (1) unless otherwise indicated. During any of the synthetic sequences it may be necessary and/or desirable to protect sensitive or reactive groups on any of the molecules concerned. The methods of addition and removal of such protecting groups are those which would conventionally be used in relation to the particular molecule-type or group being protected, for example the methods described in standard works of reference in synthetic methodology, such as Kocienski (2004) *Protecting Groups*. 4th Edn. Georg Thieme Verlag. The following processes together with the intermediates are provided as further aspects of the invention.

Thus in another aspect of the invention, compounds of formula (1), wherein Y represents $^a$-$A_1$-S-$A_2$-, $^a$-$A_5$-O-$A_6$- or $C_{2-6}$ alkylene optionally substituted with one or more $R_7$, and $R_1$ and $R_2$ represent H, may be prepared by a process which comprises reacting a compound of formula (1) with a compound of formula (II):

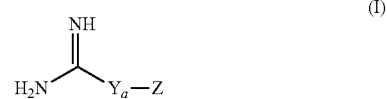

(I)

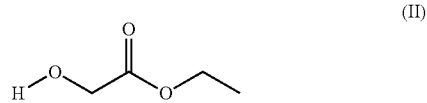

(II)

wherein $Y_a$ represents $^a$-$A_1$-S-$A_2$-, $^a$-$A_5$-O-$A_6$- or $C_{2-6}$ alkylene optionally substituted with one or more $R_7$; $A_1$, $A_2$, $A_5$, $A_6$, $R_7$, $^a$ and Z are as herein defined.

The reaction is conveniently effected by reacting a compound of formula (II) in the presence of an alkyl formate, such as ethyl formate, with a suitable base, e.g. sodium hydride, in an appropriate solvent, e.g. an ether such as diethyl ether, followed by addition of a compound of formula (1) in a suitable solvent, e.g. an alcohol such as ethanol, and subsequent heating to elevated temperature, e.g. reflux. An organic base, such as sodium ethoxide, may also be employed in the reaction.

The reaction may also be performed in the presence of ethyl-2,2,2,-trifluoroacetate to yield compounds wherein $R_1$ represents trifluoromethyl.

The intermediates of formula (1), where not commercially available, may be prepared using methods known to those skilled in the art. For example, intermediates of formula (I) wherein Y represents —S—$C_{1-3}$alkylene- or —O—$C_{1-3}$alkylene- may be prepared by reacting a thiourea —$NH_2C(S)NH_2$— or urea —$NH_2C(O)NH_2$— with an intermediate $L_1$-$C_{1-3}$alkylene-Z of formula (IV), where Z is as herein defined and $L_1$ is a suitable leaving group such as an halide e.g. bromo. The reaction may be effected at elevated temperatures in a suitable solvent such as an alcohol e.g. ethanol.

Alternatively intermediates of formula (I), wherein Y represents —$C_{1-3}$alkylene-O—, —$C_{1-3}$ alkylene-S— or optionally substituted $C_{2-6}$ alkylene may be prepared by conversion of an acetonitrile of formula Z—Y'—CN, where Y' represents —$C_{1-3}$alkylene-O—, —$C_{1-3}$alkylene-S— or optionally substituted $C_{2-6}$ alkylene. The conversion may conveniently be achieved at elevated temperature in a suitable solvent, e.g. a hydrocarbon such as toluene, in the presence of ammonium chloride and trimethyl aluminium.

In another aspect of the invention, compounds of formula (1), wherein Y represents —S—$C_{1-3}$alkylene- and $R_1$ and $R_2$ represent H, may be prepared by a process which comprises reacting a compound of formula (III) with a compound of formula (IV):

(III)

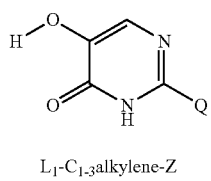

(IV)

$L_1$-$C_{1-3}$alkylene-Z wherein Q represents —SH or —S⁻W⁺, in which W⁺ is a suitable cation, $L_1$ is a suitable leaving group and Z is as herein defined. W⁺ typically represents Na⁺. $L_1$ is typically a halide such as chloro or bromo.

When Q represents —SH, the reaction is conveniently effected by stirring in a suitable solvent, e.g. N,N-dimethylformamide typically under basic conditions, e.g. in the presence of an organic base such as triethylamine.

When Q represents —S⁻W⁺, e.g. —S⁻Na⁺, the reaction may be achieved by stirring in a suitable solvent such as a cyclic ether, e.g. dioxane, and water.

In another aspect of the invention, compounds of formula (1), wherein Y represents —$S(O)_2NR_5$-$A_4$, $R_5$ and $A_4$ are as defined herein and $R_1$ and $R_2$ represent H, may be prepared by a process which comprises reacting a compound of formula (III), as defined above, with an oxidising agent such as sodium hypochlorite in the presence of an inorganic acid, e.g. HCl, to yield the corresponding sulfonyl halide derivative of formula (V):

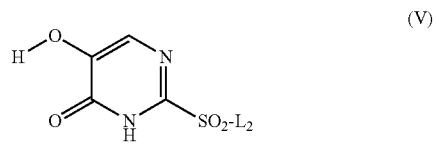

(V)

wherein $L_2$ is a suitable leaving group. $L_2$ is typically a halide such as chloro or bromo.

A compound of formula (V) may be reacted with an amine of formula $HN(R_5)$-$A_4$-Z (VI), in a suitable organic solvent using standard amide coupling methods known to those skilled in the art, such as treatment under basic conditions, e.g. NaH, to furnish a sulfonamide derivative of formula (1).

In another aspect of the invention, compounds of formula (1) wherein Y represents

or $C_{2-6}$ alkenylene and $R_1$ and $R_2$ represent H may be prepared from a compound of formula (III). For example, Q may be converted to —$SCH_3$, using methodology as defined herein, which may subsequently be treated under basic conditions, e.g. in the presence of sodium hydroxide, to yield an —OH derivative. The —OH derivative may then be converted to a suitable leaving group, e.g. by treatment with trifluoromethanesulfonic anhydride, followed by displacement with

in the presence of a suitable catalyst, such as Pd, to furnish an alkyne derivative of formula (VII):

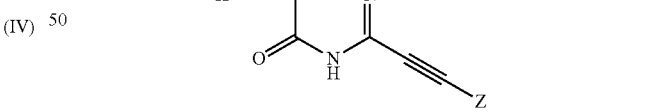

(VII)

wherein Z is as herein defined.

A compound of formula (VII) may be partially reduced, e.g. using Lindlar's catalyst, to yield an alkenylene derivative of formula (1). An alkenylene derivative of formula (1) may be cyclopropanated to furnish a further compound of formula (1) wherein Y represents

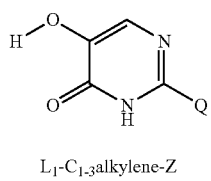, for example, by treatment with diiodomethane in the presence of zinc and copper.

In another aspect of the invention, compounds of formula (1), wherein Y represents $^{a}$-A$_1$-C(O)-A$_2$- or $^{a}$-A$_3$-C(O)NR$_3$-A$_4$, may be prepared from an intermediate of formula (VIII):

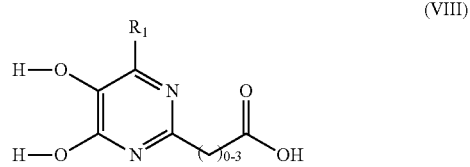

(VIII)

wherein R$_1$ is as herein defined and R$_2$ represents H.

Thus compounds according to formula (1) wherein Y represents $^{a}$A$_3$-C(O)NR$_3$-A$_4$ may be prepared by a process which comprises reacting a compound of formula (VIII) with a compound of formula HN(R$_3$)-A$_4$-Z, in a suitable organic solvent using standard amide coupling methods known to those skilled in the art. Examples of amide coupling reagents that are known in the art include carbodiimides such as dicyclohexylcarbodiimide (DCC) or 1-(3-dimethylaminopropyl)-3-ethylcarbodiimide hydrochloride (EDCI).

Compounds according to formula (1) wherein Y represents $^{a}$-A$_1$-C(O)-A$_2$ may be prepared by a process which comprises initial conversion of a compound of formula (VIII) to the corresponding Weinreb amide (—C(O)—N(CH$_3$)—O(CH$_3$)), using standard amide coupling methods, followed by reaction with a Grignard reagent, e.g. BrMg-A$_2$-Z, in a suitable organic solvent, e.g. diethyl ether. Such methodology is well known to those skilled in the art.

In another aspect of the invention, compounds of formula (1), wherein Y represents $^{a}$A$_3$-NR$_4$C(O)-A$_4$- or $^{a}$A$_3$-NR$_6$S(O)$_2$-A$_4$, may be prepared from an intermediate of formula (IX):

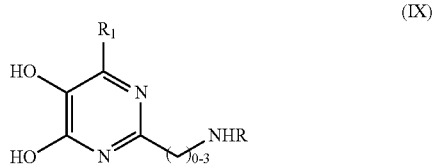

(IX)

wherein R$_1$ is as herein defined, R$_2$ represents H and R represents R$_4$ or R$_6$.

Thus compounds according to formula (1) wherein Y represents $^{a}$A$_3$-NR$_4$C(O)-A$_4$- or $^{a}$A$_3$-NR$_6$S(O)$_2$-A$_4$ may be prepared by a process which comprises reacting a compound of formula (IX) with a compound of formula L$_3$-C(O)-A$_4$-Z or L$_3$-S(O)$_2$-A$_4$-Z respectively, where L$_3$ represents a suitable leaving group such as a halide, e.g. bromo or chloro, in a suitable organic solvent, e.g. a halogenated hydrocarbon such as dichloromethane, in the presence of an organic amine, e.g. triethylamine.

Intermediates of formula (VIII) and (IX) may be prepared from commercially available materials using methods known in the art, such as step-wise conversion from 2-amino-4-chloro-5-methoxypyrimidine. For example, 2-amino-4-chloro-5-methoxypyrimidine may be treated with sodium methoxide in a suitable solvent, e.g. methanol, to give 2-amino-4,5-dimethoxypyrimidine, a protected derivative of formula (IX). 2-Amino-4,5-dimethoxypyrimidine may be treated with sodium nitrite in the presence of HCl to give the corresponding 2-chloro-4,5-dimethoxypyrimidine, which may then be treated with a cyanide reagent, e.g. potassium cyanide, in the presence of a suitable catalyst such as 4-(dimethylamino)pyridine to give 2-cyano-4,5-dimethoxypyrimidine, which may be oxidised using standard conditions such as treatment under acidic conditions, e.g. HCl, in a suitable solvent such as methanol, followed by treatment with a base, e.g. LiOH in THF/water, to provide 2-carboxy-4,5-dimethoxypyrimidine, a protected derivative of formula (VIII). Alternatively, 2-cyano-4,5-dimethoxypyrimidine may be hydrogenated, e.g. by treatment with hydrogen in the presence of a suitable catalyst such as palladium on carbon, to give 2-aminomethyl-4,5-dimethoxypyrimidine, a further protected derivative of formula (IX).

By means of further example, 2-chloro-4,5-dimethoxypyrimidine may also be treated with dimethylmalonate in the presence of a suitable base, e.g. sodium hydride, with subsequent heating in the presence of hydronium to give 2-carboxymethyl-4,5-dimethoxypyrimidine, a further protected derivative of formula (VIII).

In a further example, 2-carboxy-4,5-dimethoxypyrimidine (VIII) may be reduced, e.g. using a reducing agent such as LiAlH$_4$ to give 2-hydroxymethyl-4,5-dimethoxypyrimidine, which may be treated with methylsulfonyl chloride in the presence of an organic base, e.g. triethylamine, followed by treatment with sodium sulphide to give 2-thiomethyl-4,5-dimethoxypyrimidine, which may be oxidised to 2-chlorosulfonylmethyl-4,5-dimethoxypyrimidine, which may be used in a similar manner to intermediates of formula (V).

It will be understood that any compound of formula (1) initially obtained from any of the above processes may, where appropriate, subsequently be elaborated into a further compound of formula (1) by techniques known from the art. By way of example, a compound of formula (1) wherein R$_2$ represents H may be converted to a further compound of formula (1) wherein R$_2$ represents C$_{1-6}$ alkyl by reaction with a suitable alkylating agent, e.g. methyl iodide, typically under basic conditions, e.g. in the presence of an inorganic base such as potassium carbonate, in a suitable solvent, e.g. N,N-dimethylformamide. By way of further example, a compound of formula (1) wherein Y represents $^{a}$-A$_1$-S-A$_2$-, may be converted to a further compound of formula (1), wherein Y represents $^{a}$-A$_1$-S(O)$_{1-2}$-A$_2$-by reaction with a suitable oxidising agent such as 3-chloroperoxybenzoic acid (m-CPBA). By way of another example, a compound of formula (1) wherein Y represents $^{a}$-A$_1$-C(O)-A$_2$ may be converted to a further compound of formula (1), wherein Y represents C$_{2-6}$ alkylene substituted with a C$_{1-6}$ alkylene chain attached to the same carbon atom to form a spiro-fused C$_3$ cycloalkyl ring, i.e.:

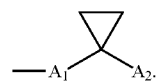

The reaction may conveniently be achieved by initial conversion to the $^{a}$-A$_1$-C(=CH$_2$)-A$_2$ derivative, for example by reaction with Tebbe's reagent, followed by treatment with diiodomethane in the presence of zinc and copper.

It will be further understood that a deprotection may be the final step in the synthesis of a compound of formula (1) and the processes according to the invention described hereinafter are to be understood to extend to such removal of protecting groups. The protecting groups may be removed using methods well known to those skilled in the art. For example, an hydroxy protecting group such as tetrahydro-2H-pyran-2-yl may be removed under acidic conditions such as in the presence of an organic acid, e.g. p-toluenesulfonic acid, in a suitable solvent, e.g. an alcohol such as methanol, or in the presence of an inorganic acid such as HCl in a suitable solvent such as a cyclic ether, e.g. dioxane. Alternatively, an hydroxy protecting group such as methyl may be removed using boron tribromide in an halogenated solvent such as dichloromethane.

The compounds of formula (1) above may be converted to a pharmaceutically acceptable salt thereof, preferably an acid addition salt such as a hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-naphthoate (xinafoate), methanesulphonate or p-toluenesulphonate salt.

Novel intermediates form a further aspect of the invention.

The invention will now be described in more detail by way of example only.

1. SYNTHETIC METHODOLOGIES

The methods used for synthesis of the compounds of the invention are illustrated by the general schemes below and the preparative examples that follow. The starting materials and reagents used in preparing these compounds are available from commercial suppliers. These general schemes are merely illustrative of methods by which the compounds of this invention can be synthesised, and various modifications to these schemes can be made and will be suggested to one skilled in the art having referred to this disclosure.

Nuclear magnetic resonance (NMR) spectra were recorded at 400 MHz; the chemical shifts (δ) are reported in parts per million. Spectra were recorded using a Bruker 400 Avance instrument fitted with a 5 mm BBFO probe or DUL probe. Instrument control was by Bruker TopSpin 2.1 software, unless stated otherwise.

Purity was assessed using UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C. Mobile phases typically consisted of acetonitrile or MeOH mixed with water containing either 0.05% formic acid or 0.025% ammonia. Mass spectra were recorded with a Waters SQD single quadrupole mass spectrometer using atmospheric pressure ionisation, unless stated otherwise.

Compounds were purified using normal phase chromatography on silica or alumina, or by reverse phase chromatographic methods, using Biotage or Isolute KPNH Cartridge, SCX cartridge and SCX-2 solid phase extraction cartridges.

Preparative HPLC was performed using an Agilent Technologies 1100 Series system typically using Waters 19 mm id×100 mm long C18 columns such as XBridge or SunFire 5 μm materials at 20 mL/min. Mobile phases typically consisted of acetonitrile or MeOH mixed with water containing either 0.1% formic acid or 0.1% ammonia, unless stated otherwise.

In the following descriptions "room temperature" ranges from 20° C. to 25° C.

Abbreviations

AIBN Azobisisobutyronitrile
$AlMe_3$ Trimethylaluminium
DCM Dichloromethane
DMF Dimethyl formamide
DMSO Dimethyl sulfoxide
$d_6$-DMSO Deuterated dimethyl sulfoxide
Et Ethyl
EtOAc Ethyl acetate
EtOH Ethanol
$Et_2O$ Diethyl ether
$Et_3N$ Triethylamine
LCMS Liquid chromatography mass spectrum
LDA Lithium diisopropylamide
MS Mass spectrum
Me Methyl
MeOD Deuterated MeOH
MeOH Methanol
MTBE tert-butylmethyl ether
NaOEt Sodium ethoxide
NBS N-bromosuccinimide
NMR Nuclear magnetic resonance
Ph Phenyl
PTSA para-Toluene sulfonic acid
Rt room temperature
THF Tetrahydrofuran Schemes 1-5 (shown in 1.1 to 1.5 below) serve to illustrate the methodologies that may be used to synthesize the exemplified compounds of formula (1) and intermediates used in the synthesis of the exemplified compounds of formula (1).

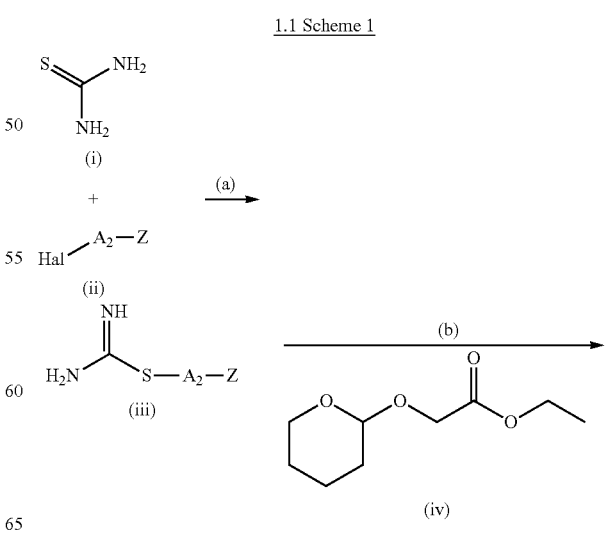

1.1 Scheme 1

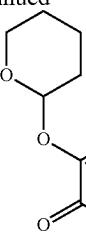

(v)

↓(c)

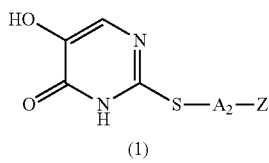

(1)

(a) EtOH, reflux
(bi) NaH, Ethyl formate, Et₂O; (bii) EtOH, reflux
(c) HCl, Dioxane or PTSA·H₂O, MeOH.

Compounds according to formula (1), wherein Y represents —S—C$_{1-3}$alkylene-, may be prepared according to Scheme 1:

Wherein Hal represents a halide e.g. chloro or bromo, A$_2$ represents optionally substituted C$_{1-3}$alkylene and Z is as defined herein and R$_1$ and R$_2$ represent H.

1.2 Scheme 2.

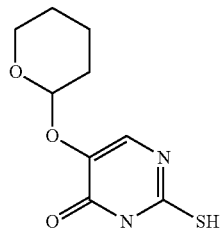

(vi)

CAS 894421-78-4

(b)↓

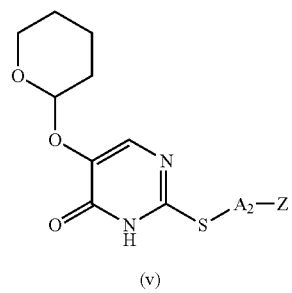

(v)

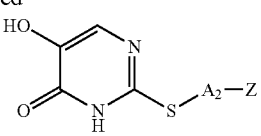

(1)

(a) Z—A$_2$—Hal, Et$_3$N, DMF
(b) HCl, Dioxane or PTSA, H$_2$O, MeOH.

Alternatively compounds according to Formula (1), wherein Y represents —S—C$_{1-3}$alkylene-, may be prepared according to Scheme 2:

Wherein Hal represents a halide e.g. chloro or bromo, A$_2$ represents optionally substituted C$_{1-3}$alkylene and Z is as defined herein and R$_1$ and R$_2$ represent H.

1.3 Scheme 3.

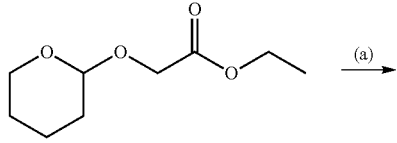

(iv)

CAS 61675-94-3

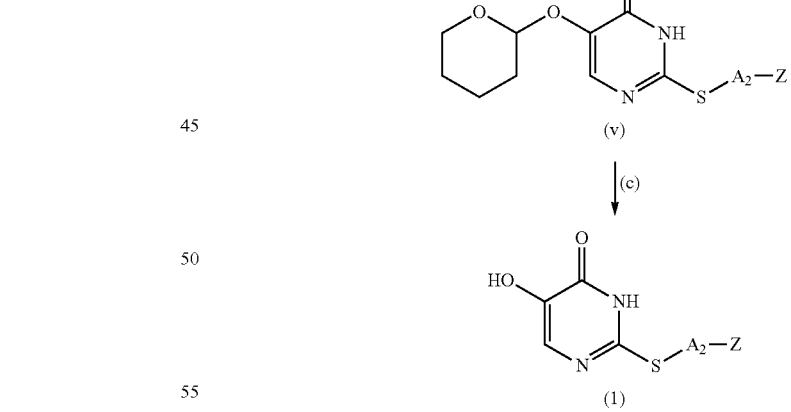

(v)

↓(c)

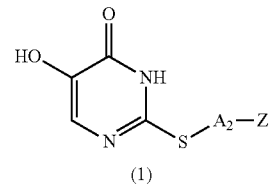

(1)

a) sodium, thiourea, ethyl formate, toluene;
(b) Z—A$_2$—Hal, dioxane and water;
(c) HCl, Dioxane or PTSA·H$_2$O, MeOH.

Alternatively compounds according to Formula (1), wherein Y represents —S—C$_{1-3}$alkylene-, may be prepared according to Scheme 3:

Wherein Hal represents a halide e.g. chloro or bromo, A$_2$ represents optionally substituted C$_{1-3}$alkylene and Z is as defined herein and R$_1$ and R$_2$ represent H.

1.4 Scheme 4.

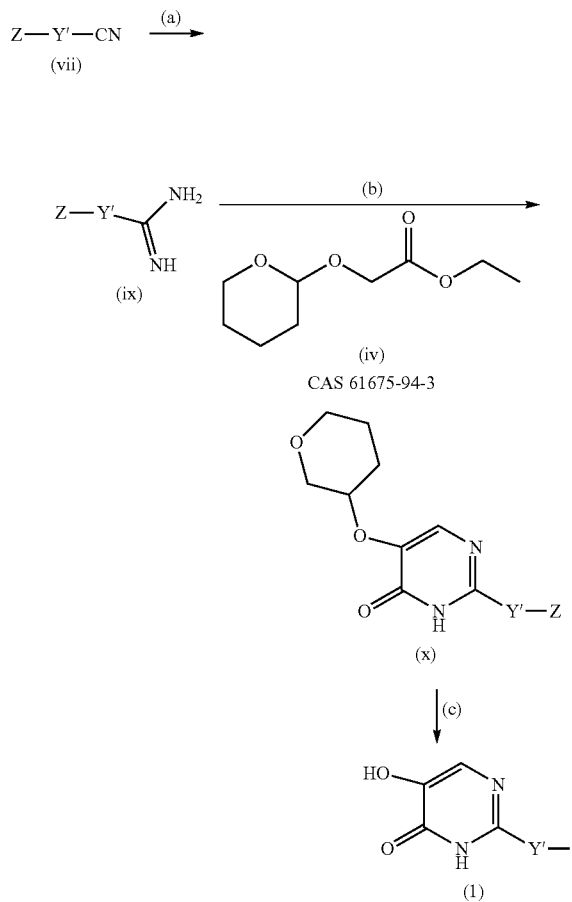

(a) NH₄Cl, AlMe₃, toluene;
(b) i. NaH, ethyl formate, Et₂O ii. NaOEt, EtOH or AlMe₃, THF;
(c) HCl, Dioxane or PTSA. H₂O, MeOH.

Compounds according to formula (1), wherein Y represents $C_{1-3}$alkylene-S—, —$C_{1-3}$alkylene-S— or optionally substituted $C_{2-6}$alkylene may be prepared according to Scheme 4:

Wherein Y' represents —$C_{1-3}$alkylene-S—, $C_{1-3}$alkylene-S— or optionally substituted $C_{2-6}$alkylene, Z is as defined herein and $R_1$ and $R_2$ represent H.

1.5 Scheme 5.

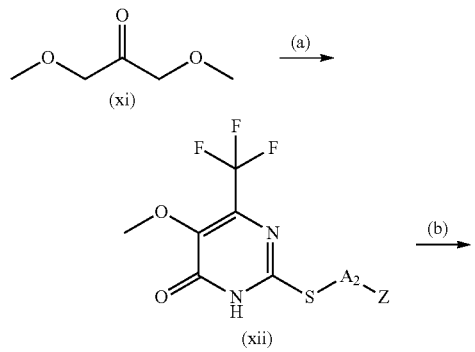

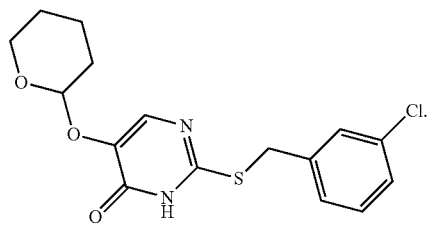

(a) LDA, THF; F₃CCO₂Et; Z—A₂—S—C(=NH)(NH₂), EtOH; (b) BBr₃

Compounds according to Formula (1), wherein Y represents —S—$C_{1-3}$alkylene- and $R_1$ represents halo$C_{1-6}$alkyl, may be prepared according to Scheme 5:
wherein A₂ and Z are as defined herein and $R_2$ represents H.

1.1.1 Intermediate 1 (Prepared According to Scheme 1 Step (a))

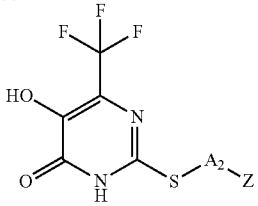

3-(5-Methyl-1,2,4-oxadiazol-3-yl)benzyl carbamidothioate hydrobromide

To a solution of 1-(bromomethyl)-3-chlorobenzene (2.7 g, 13.1 mmol) in EtOH (Volume: 100 ml) was added thiourea (1 g, 13.1 mmol) and the reaction stirred at reflux overnight. The reaction mixture was concentrated to yield 3-chlorobenzyl carbamimidothioate, HBr in quauntitative yield.
MS ES⁺: 201

1.1.2 Intermediate 2 (Prepared According to Scheme 1 Step (b)

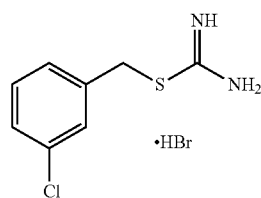 [SMILES: N=C(N)SCc1cccc(Cl)c1 ; Br]

2-[(3-Chlorobenzyl)sulfanyl]-5-(tetrahydro-2H-pyran-2-yloxy)pyrimidin-4(3H)-one

To a suspension of sodium hydride (0.26 g, 6.39 mmol) in Et₂O (10 ml) was added ethyl formate (0.40 g, 5.33 mmol) and then ethyl 2-(tetrahydro-2H-pyran-2-yloxy)acetate (1.00 g, 5.33 mmol) drop-wise and the mixture stirred at reflux for 2 hours. 3-Chlorobenzyl carbamimidothioate HBr salt (Int 1) (1.5 g, 5.33 mmol) was then added followed by EtOH (10 ml). The ether was removed in vacuo and then the resulting ethanolic solution heated at reflux for 4 hours. The reaction mixture was evaporated and the resulting solid purified by column chromatography (SiO₂: 0-10% MeOH in DCM) to yield 2-[(3-chlorobenzyl)sulfanyl]-5-(tetrahydro-2H-pyran-2-yloxy)pyrimidin-4(3H)-one (524 mg, 28%).

¹H NMR (400 MHz, CD₂Cl₂): δ 7.79 (s, 1H), 7.45 (s, 1H), 7.18-7.39 (m, 3H), 5.41-5.51 (m, 1H), 4.42 (s, 2H), 3.83-4.02 (m, 1H), 3.56-3.69 (m, 1H), 1.44-2.18 (m, 6H).

MS ES⁻: 351.

The compounds according to Intermediates 3 to 15 were prepared in a similar manner to the methodology described for Intermediate 3 and according to Scheme 1 step (a) and step (b) using commercially available reagents unless otherwise stated.

1.1.3 Intermediate 3

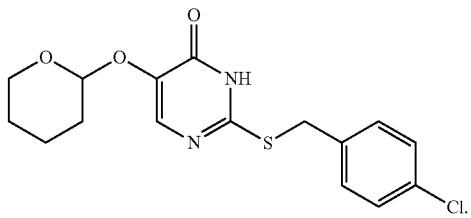 [SMILES: O=c1[nH]c(SCc2ccc(Cl)cc2)ncc1OC1CCCCO1]

2-[(4-Chlorobenzyl)sulfanyl]-5-(tetrahydro-2H-pyran-2-yloxy)pyrimidin-4(3H)-one

Prepared from 1-(bromomethyl)-4-chlorobenzene.

1.1.4 Intermediate 4

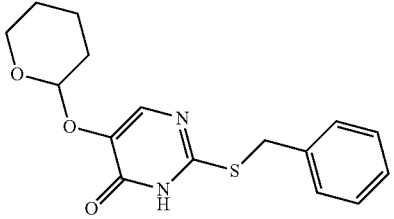 [SMILES: O=c1[nH]c(SCc2ccccc2)ncc1OC1CCCCO1]

2-(Benzylsulfanyl)-5-(tetrahydro-2H-pyran-2-yloxy)pyrimidin-4(3H)-one

Prepared from 1-(bromomethyl)benzene.

¹H NMR (400 MHz, DMSO-d₆): δ 7.70 (s, 1H), 7.11-7.50 (m, 5H), 5.44 (m, 1H), 4.37 (s, 2H), 3.76-3.86 (m, 1H) 3.48-3.58 (m, 1H), 1.35-1.98 (m, 6H).

MS ES⁺: 319.

Alternatively Intermediate 4 may be prepared according to the methodology described in Scheme 2 step (a):

To a solution of 2-sulfanyl-5-(tetrahydro-2H-pyran-2-yloxy)pyrimidin-4(3H)-one (315 mg, 1.38 mmol) in DMF (15 ml) at 0° C. was added triethylamine (0.20 ml, 1.38 mmol) and then (bromomethyl)benzene (236 mg, 1.38 mmol) drop-wise. The reaction mixture was allowed to stir at this temperature for 2 hours before being quenched with water and extracted with EtOAc. The organics were isolated and evaporated. The residue was purified by column chromatography ((SiO₂: 0-5% MeOH in DCM) to yield 2-(benzylsulfanyl)-5-(tetrahydro-2H-pyran-2-yloxy)pyrimidin-4(3H)-one (55 mg, 13%).

1.1.5 Intermediate 5

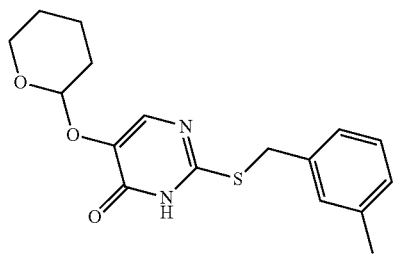 [SMILES: Cc1cccc(CSc2ncc(OC3CCCCO3)c(=O)[nH]2)c1]

2-[(3-Methylbenzyl)sulfanyl]-5-(tetrahydro-2H-pyran-2-yloxy)pyrimidin-4(3H)-one

Prepared from 1-(bromomethyl)-3-methylbenzene.
MS ES⁺: 333.

1.1.6 Intermediate 6

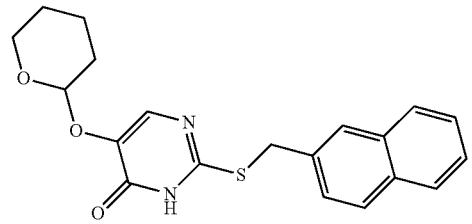 [SMILES: O=c1[nH]c(SCc2ccc3ccccc3c2)ncc1OC1CCCCO1]

2-[(Naphthalen-2-ylmethyl)sulfanyl]-5-(tetrahydro-2H-pyran-2-yloxy)pyrimidin-4(3H)-one Prepared from 2-(bromomethyl)naphthalene.
MS ES⁺: 369.

1.1.7 Intermediate 7

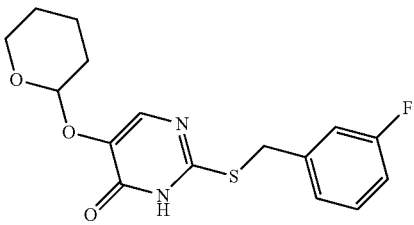 [SMILES: O=c1[nH]c(SCc2cccc(F)c2)ncc1OC1CCCCO1]

2-[(3-Fluorobenzyl)sulfanyl]-5-(tetrahydro-2H-pyran-2-yloxy)pyrimidin-4(3H)-one

Prepared from 1-(bromomethyl)-3-fluorobenzene.
MS ES⁺: 337.

1.1.8 Intermediate 8

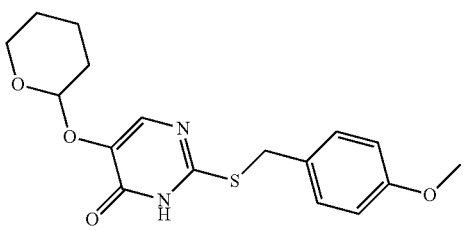 [SMILES: COc1ccc(CSc2ncc(OC3CCCCO3)c(=O)[nH]2)cc1]

2-[(4-Methoxybenzyl)sulfanyl]-5-(tetrahydro-2H-pyran-2-yloxy)pyrimidin-4(3H)-one Prepared from 1-(bromomethyl)-4-methoxybenzene.
MS ES⁺: 349.

1.1.9 Intermediate 9

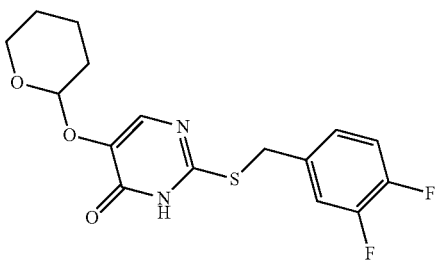 [SMILES: O=c1[nH]c(SCc2ccc(F)c(F)c2)ncc1OC1CCCCO1]

2-[(3,4-Difluorobenzyl)sulfanyl]-5-(tetrahydro-2H-pyran-2-yloxy)pyrimidin-4(3H)-one Prepared from 1-(bromomethyl)-3,4-difluorobenzene.
¹H NMR (400 MHz, DMSO-d₆): δ 7.68 (s, 1H), 7.49 (m, 1H), 7.31-7.43 (m, 1H), 7.28 (m, 1H), 5.43 (m, 1H), 4.35 (s, 2H), 3.72-3.93 (m, 1H), 3.45-3.60 (m, 1H), 1.66-1.92 (m, 3H), 1.43-1.66 (m, 3H).
MS ES⁺: 355.

1.1.10 Intermediate 10

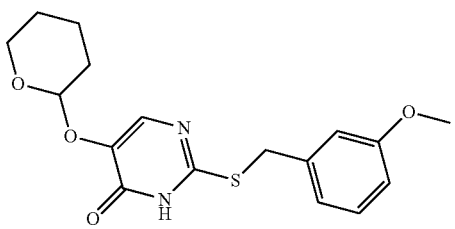 [SMILES: COc1cccc(CSc2ncc(OC3CCCCO3)c(=O)[nH]2)c1]

2-[(3-Methoxybenzyl)sulfanyl]-5-(tetrahydro-2H-pyran-2-yloxy)pyrimidin-4(3H)-one Prepared from 1-(bromomethyl)-3-methoxybenzene.
MS ES⁺: 349.

1.1.11 Intermediate 11

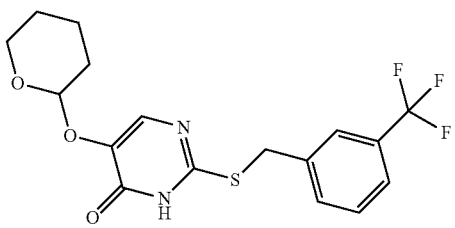 [SMILES: O=c1[nH]c(SCc2cccc(C(F)(F)F)c2)ncc1OC1CCCCO1]

5-(Tetrahydro-2H-pyran-2-yloxy)-2-{[3-(trifluoromethyl)benzyl]sulfanyl}pyridin-4(3H)-one Prepared from 1-(bromomethyl)-3-trifluoromethylbenzene.
¹H NMR (400 MHz, DMSO-d₆): 7.69 (s, 1H), 7.16-7.45 (m, 3H), 5.44 (m, 1H), 4.37 (s, 2H), 3.73-3.89 (m, 1H), 3.44-3.58 (m, 1H), 1.66-1.96 (m, 3H), 1.44-1.65 (m, 3H).
MS ES⁻: 385.

1.1.12 Intermediate 12

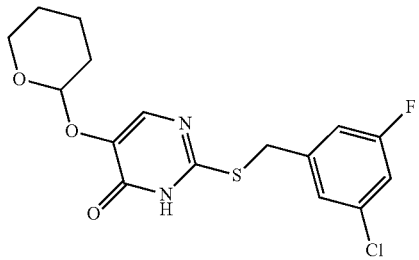 [SMILES: O=c1[nH]c(SCc2cc(F)cc(Cl)c2)ncc1OC1CCCCO1]

2-[(3-Chloro-5-fluorobenzyl)sulfanyl]-5-(tetrahydro-2H-pyran-2-yloxy)pyrimidin-4(3H)-one Prepared from 1-(bromomethyl)-3-chloro-5-fluorobenzene.
MS ES⁻: 369.

1.1.13 Intermediate 13

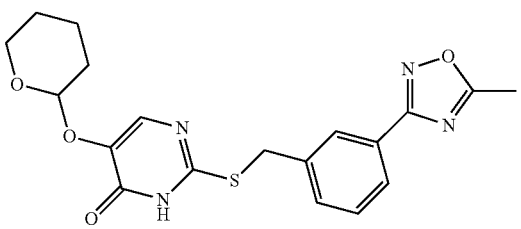 [SMILES: Cc1nc(-c2cccc(CSc3ncc(OC4CCCCO4)c(=O)[nH]3)c2)no1]

2-{[3-(5-Methyl-1,2,4-oxadiazol-3-yl)benzyl]sulfanyl}-5-(tetrahydro-2H-pyran-2-yloxy)pyrimidin-4(3H)-one Prepared from 3-(3-(bromomethyl)phenyl)-5-methyl-1,2,4-oxadiazole.
MS ES+: 401.

1.1.14 Intermediate 14

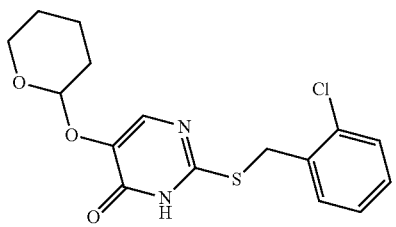 [SMILES: O=c1[nH]c(SCc2ccccc2Cl)ncc1OC1CCCCO1]

2-[(2-Chlorobenzyl)sulfanyl]-5-(tetrahydro-2H-pyran-2-yloxy)pyrimidin-4(3H)-one
Prepared from 1-(bromomethyl)-2-chlorobenzene.
MS ES+: 353.

1.1.15 Intermediate 15

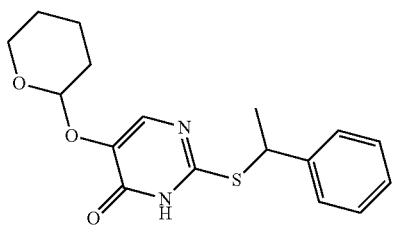 [SMILES: CC(Sc1ncc(OC2CCCCO2)c(=O)[nH]1)c1ccccc1]

2-[(1-Phenylethyl)sulfanyl]-5-(tetrahydro-2H-pyran-2-yloxy)pyrimidin-4(3H)-one

Prepared from (1-bromoethyl)benzene.
MS ES+: 333.

1.3.1 Intermediate 16 (Prepared According to Scheme 3 Step a)

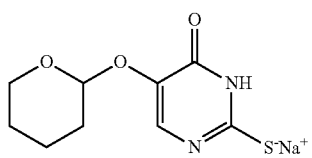

Sodium-6-oxo-5-(tetrahydro-2H-pyran-2-yloxy)-1,6-dihydropyrimidine-2-thiolate

A 100 ml round-bottomed flask was charged with diced sodium (2.30 g, 0.1 mol), in toluene (30 ml) to give a colourless suspension. A mixture of ethyl formate (8.14 ml, 0.10 mol) and ethyl 2-(tetrahydro-2H-pyran-2-yloxy)acetate (9.9 ml, 0.10 mol) were added drop-wise, taking care to make sure the temperature did not exceed 30° C. The reaction was stirred at room temperature overnight by which point a brown viscous oil had settled out with some sodium remaining. The toluene was decanted off and ethanol (15 ml) was added and the reaction was stirred until remaining sodium had dissolved. Carbamimidothioic acid (7.61 g, 0.10 mol) was added and the reaction was stirred at room temperature for 1 hour and then heated to reflux for 4 hours. The reaction was cooled and diluted with water (50 ml) and diisopropyl ether and the aqueous layer separated. The diisopropyl ether layer was washed with water and the combined aqueous layers were washed with diisopropyl ether and then made up to 100 ml and used crude in the next step.

1.3.2 Intermediate 17 (Prepared According to Scheme 3 Step (b))

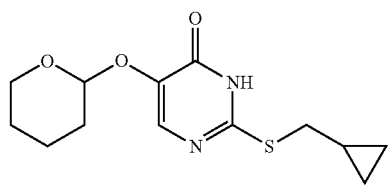 [SMILES: O=c1[nH]c(SCC2CC2)ncc1OC1CCCCO1]

2-[(Cyclopropylmethyl)sulfanyl]-5-(tetrahydro-2H-pyran-2-yloxy)pyrimidin-4(3H)-one To a crude aqueous solution of sodium 6-oxo-5-(tetrahydro-2H-pyran-2-yloxy)-1,6-dihydropyrimidine-2-thiolate (Intermediate 16) (2.50 g, 10 mmol) in water (10.0 ml) was added dioxane (10 ml) and (bromomethyl)cyclopropane (945 mg, 7.00 mmol) the reaction was stirred for one hour after which solid had precipitated. This was filtered off, washed with water and ether and dried to yield pure 2-[(cyclopropylmethyl)sulfanyl]-5-(tetrahydro-2H-pyran-2-yloxy)pyrimidin-4(3H)-one (452 mg, 16% yield).
$^1$H NMR (400 MHz, DMSO-$d_6$): δ 12.63 (br, s, 1H), 7.40 (br, s, 1H), 5.18 (br, s, 1H), 3.46-3.66 (m, 1H), 3.19-3.34 (m, 1H), 2.80 (m, 2H), 1.42-1.73 (m, 3H), 1.15-1.43 (m, 3H), 0.86 (m, 1H), 0.20-0.41 (m, 2H), 0.04 (m, 2H).
MS ES+: 283.

The compounds according to Intermediates 18 to 31 were prepared in a similar manner to the methodology described for Intermediate 17 and according to Scheme 3 step (b) using commercially available alkylating reagents unless otherwise stated.

1.3.3 Intermediate 18

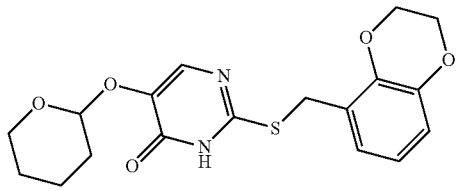 [SMILES: O=c1[nH]c(SCc2cccc3c2OCCO3)ncc1OC1CCCCO1]

2-[(2,3-Dihydro-1,4-benzodioxin-5-ylmethyl)sulfa-
nyl]-5-(tetrahydro-2H-pyran-2-yloxy)pyrimidin-4
(3H)-one ¹H NMR (400 MHz, DMSO-d₆): δ 7.68 (s, 1H), 6.91 (m, 1H), 6.59-6.87 (m, 2H), 5.43 (m, 1H), 4.05-4.48 (m, 6H), 3.75-3.91 (m, 1H), 3.47-3.55 (m, 1H), 1.65-1.95 (m, 3H), 1.35-1.67 (m, 3H).
MS ES⁺: 377.

1.3.4 Intermediate 19

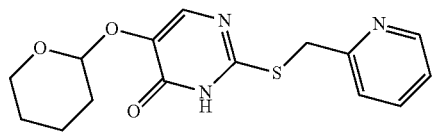 [SMILES: O=c1[nH]c(SCc2ccccn2)ncc1OC1CCCCO1]

2-(Pyridin-2-ylmethylthio)-5-(tetrahydro-2H-pyran-
2-yloxy)pyrimidin-4(3H)-one

MS ES⁺: 320.

1.3.5 Intermediate 20

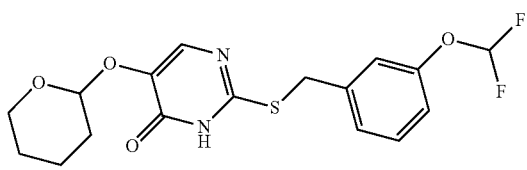 [SMILES: O=c1[nH]c(SCc2cccc(OC(F)F)c2)ncc1OC1CCCCO1]

2-(3-(Difluoromethoxy)benzylthio)-5-(tetrahydro-
2H-pyran-2-yloxy)pyrimidin-4(3H)-one

MS ES⁺: 385.

1.3.6 Intermediate 21

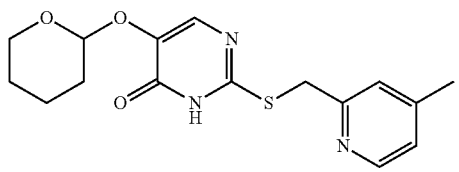 [SMILES: Cc1ccnc(CSc2ncc(OC3CCCCO3)c(=O)[nH]2)c1]

2-((4-Methylpyridin-2-yl)methylthio)-5-(tetrahydro-
2H-pyran-2-yloxy)pyrimidin-4(3H)-one

MS ES⁺: 334.

1.3.7 Intermediate 22

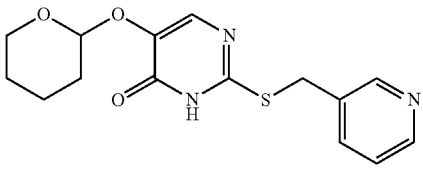 [SMILES: O=c1[nH]c(SCc2cccnc2)ncc1OC1CCCCO1]

2-(Pyridin-3-ylmethylthio)-5-(tetrahydro-2H-pyran-
2-yloxy)pyrimidin-4(3H)-one

MS ES⁺: 320.

1.3.8 Intermediate 23

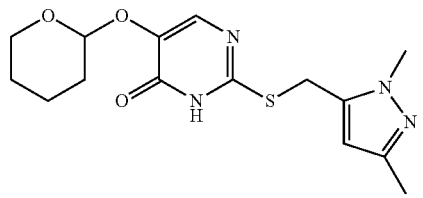 [SMILES: Cc1cc(CSc2ncc(OC3CCCCO3)c(=O)[nH]2)n(C)n1]

2-(((1,3-Dimethyl-1H-pyrazol-5-yl)methylthio)-5-
(tetrahydro-2H-pyran-2-yloxy)pyrimidin-4(3H)-one

MS ES⁺: 337.

1.3.9 Intermediate 24

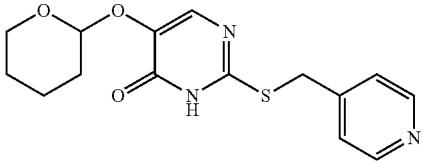 [SMILES: O=c1[nH]c(SCc2ccncc2)ncc1OC1CCCCO1]

2-(Pyridin-4-ylmethylthio)-5-(tetrahydro-2H-pyran-
2-yloxy)pyrimidin-4(3H)-one

MS ES⁺: 320.

1.3.10 Intermediate 25

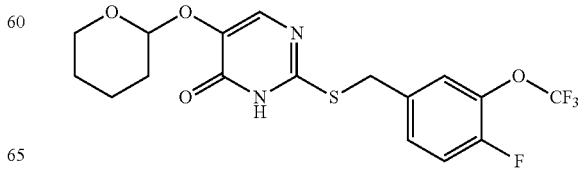

2-(4-Fluoro-3-(trifluoromethoxy)benzylthio)-5-(tetrahydro-2H-pyran-2-yloxy)pyrimidin-4(3H)-one

MS ES+: 421.

1.3.11 Intermediate 26

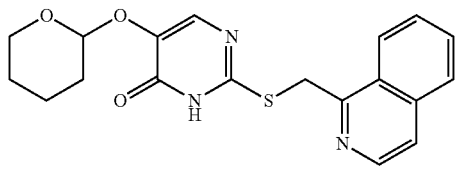 [SMILES: O=c1[nH]c(SCc2nccc3ccccc23)ncc1OC1CCCCO1]

2-[(Isoquinolin-1-ylmethyl)sulfanyl]-5-(tetrahydro-2H-pyran-2-yloxy)pyrimidin-4(3H)-one

MS ES+370,

1.3.12 Intermediate 27

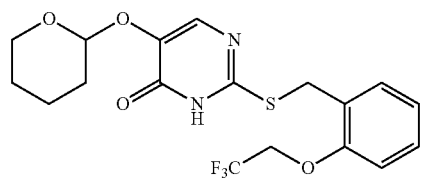 [SMILES: O=c1[nH]c(SCc2ccccc2OCC(F)(F)F)ncc1OC1CCCCO1]

5-(Tetrahydro-2H-pyran-2-yloxy)-2-{[2-(2,2,2-trifluoroethoxy)benzyl]sulfanyl}pyrimidin-4(3H)-one MS ES+417.
Prepared from 1-(bromomethyl)-2-(2,2,2-trifluoroethoxy)benzene:
To a solution of 1-methyl-2-(2,2,2-trifluoroethoxy)benzene (0.8 g, 4.2 mmol, CAS RN 80054-83-7) in carbon tetrachloride (25 ml) was added AIBN (0.07 g, 0.4 mmol) and N-bromo succinimide (0.82 g, 4.6 mmol) at room temperature and the reaction was stirred at reflux temperature for 3 hours. The reaction mixture was washed with saturated sodium bicarbonate solution (25 ml) followed by brine solution (25 ml). The organic layer was dried and evaporated to give crude product which was purified by column chromatography (SiO$_2$: 0-3% EtOAc in petrol) and product fractions concentrated to yield 1-(bromomethyl)-2-(2,2,2-trifluoroethoxy)benzene (0.6 g, 53%).
$^1$H NMR (400 MHz, DMSO-d6): δ 7.47-7.45 (d, 1H), 7.41-7.35 (t, 1H), 7.16-7.14 (d, 1H), 7.06-7.02 (t, 1H), 4.91-4.82 (m, 2H), 4.64 (s, 2H).

1.3.13 Intermediate 28

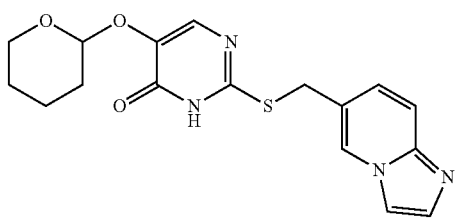 [SMILES: O=c1[nH]c(SCc2ccc3nccn3c2)ncc1OC1CCCCO1]

2-[(Imidazo[1,2-a]pyridin-6-ylmethyl)sulfanyl]-5-(tetrahydro-2H-pyran-2-yloxy)pyrimidin-4(3H)-one

MS ES+359.

1.3.14 Intermediate 29

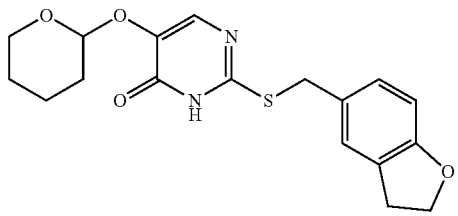 [SMILES: O=c1[nH]c(SCc2ccc3c(c2)CCO3)ncc1OC1CCCCO1]

2-[(2,3-Dihydro-1-benzofuran-5-ylmethyl)sulfanyl]-5-(tetrahydro-2H-pyran-2-yloxy)pyrimidin-4(3H)-one

1.3.15 Intermediate 30

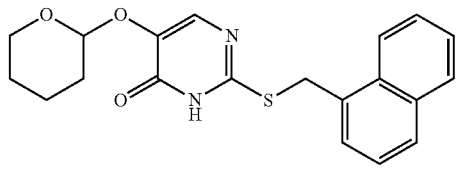 [SMILES: O=c1[nH]c(SCc2cccc3ccccc23)ncc1OC1CCCCO1]

2-[(Naphthalen-1-ylmethyl)sulfanyl]-5-(tetrahydro-2H-pyran-2-yloxy)pyrimidin-4(3H)-one MS ES+ 284 (M-pyran).

1.3.16 Intermediate 31

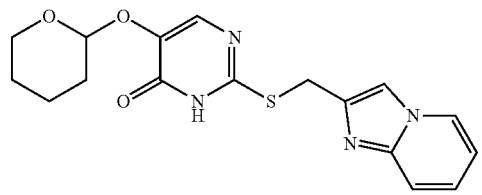 [SMILES: O=c1[nH]c(SCc2cn3ccccc3n2)ncc1OC1CCCCO1]

2-[(Imidazo[1,2-a]pyridin-2-ylmethyl)sulfanyl]-5-(tetrahydro-2H-pyran-2-yloxy)pyrimidin-4(3H)-one

MS ES+359.

1.4.1 Intermediate 32 (Prepared According to Scheme 4 Step (a))

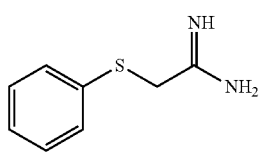 [SMILES: N=C(N)CSc1ccccc1]

2-(Phenylsulfanyl)ethanimidamide

To a suspension of ammonium chloride (1.33 g, 24.8 mmol) in toluene (10 ml) under $N_2$ at 0° C. was added trimethyl aluminium (12.1 ml, 24.1 mmol). The reaction mixture was stirred at RT for 2 hours. To this flask was then added a solution of 2-(phenylthio)acetonitrile (1 g, 6.70 mmol) in toluene (10 ml). The reaction was then stirred at 110° C. overnight. The reaction mixture was allowed to cool and then poured onto a slurry of silica in DCM. The slurry was stirred for 15 minutes and then filtered. The resulting filtrate was concentrated under vacuum and taken up in DCM. The organic mixture was washed with 1M HCl. The aqueous layer was concentrated under vacuum, taken up in water and then basified with 2M NaOH. The aqueous mixture was extracted with DCM. The organic layer was concentrated to yield 2-(phenylsulfanyl)ethanimidamide (850 mg, 5.11 mmol, 76% yield).

$^1$H NMR (400 MHz, $CD_2Cl_2$): δ 7.31-7.51 (m, 4H), 7.18-7.31 (m, 1H), 5.13 (br. s., 3H) and 3.67 (s, 2H).

MS ES$^+$: 167.

1.4.2 Intermediate 33 (Prepared According to Scheme 4 Step (b))

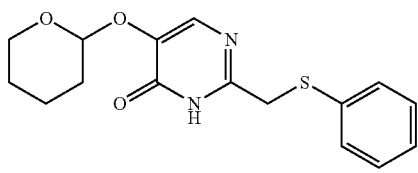 [SMILES: O=c1[nH]c(CSc2ccccc2)ncc1OC1CCCCO1]

2-[(Phenylsulfanyl)methyl]-5-(tetrahydro-2H-pyran-2-yloxy)pyrimidin-4(3H)-one

To a suspension of sodium hydride (182 mg, 4.55 mmol) in diethyl ether (10 ml) was added ethyl formate (281 mg, 3.79 mmol) followed by ethyl 2-(tetrahydro-2H-pyran-2-yloxy)acetate (713 mg, 3.79 mmol). The resulting mixture was stirred under reflux for 1.5 hours. To this mixture was then added a pre-mixed solution of 2-(phenylsulfanyl)ethanimidamide (Intermediate 32) (630 mg, 3.79 mmol) and sodium ethoxide (1.23 g, 3.79 mmol) in EtOH (10 ml). The ether was removed under vacuum and the resulting suspension stirred at reflux for 3 hours. The reaction mixture was concentrated and purified by column chromatography ($SiO_2$: 0-10% MeOH in DCM) to yield 2-[(phenylsulfanyl)methyl]-5-(tetrahydro-2H-pyran-2-yloxy)pyrimidin-4(3H)-one (275 mg, 23% yield).

MS ES$^-$: 317.

The compounds according to Intermediates 34 to 35 were prepared in a similar manner to the methodology described for Intermediate 32 and 33 and according to Scheme 4 steps (a) and (b) using commercially available reagents unless otherwise stated.

1.4.3 Intermediate 34

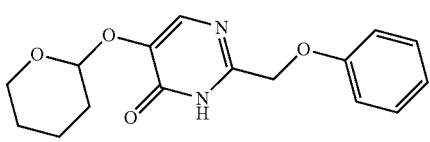 [SMILES: O=c1[nH]c(COc2ccccc2)ncc1OC1CCCCO1]

2-(Phenoxymethyl)-5-(tetrahydro-2H-pyran-2-yloxy)pyrimidin-4(3H)-one

Prepared from phenoxyacetonitrile.

MS ES$^+$: 303.

1.4.4 Intermediate 35

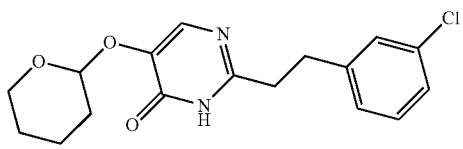 [SMILES: O=c1[nH]c(CCc2cccc(Cl)c2)ncc1OC1CCCCO1]

2-[2-(3-Chlorophenyl)ethyl]-5-(tetrahydro-2H-pyran-2-yloxy)pyrimidin-4(3H)-one

Prepared from 3-(3-chlorophenyl)propanenitrile $^1$H NMR (400 MHz, $CD_2Cl_2$): 7.79 (s, 1H), 7.45 (s, 1H), 7.19-7.37 (m, 4H), 5.44 (m, 1H), 4.42 (s, 2H), 3.87-3.98 (m, 2H), 3.57-3.72 (m, 2H), 1.44-2.14 (m, 6H).

1.4.5 Intermediate 36 (Prepared According to Scheme 4 Step (b))

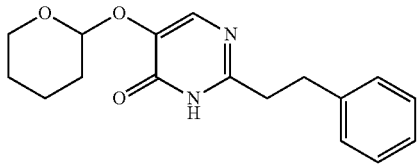 [SMILES: O=c1[nH]c(CCc2ccccc2)ncc1OC1CCCCO1]

2-(2-Phenylethyl)-5-(tetrahydro-2H-pyran-2-yloxy)pyrimidin-4(3H)-one

To a suspension of sodium hydride (29.0 mg, 0.74 mmol) in diethyl ether (2 ml), ethyl formate (45.0 mg, 0.61 mmol) was added. Ethyl-2-(tetrahydro-2H-pyran-2-yloxy)acetate (115 mg, 0.61 mmol) was then added dropwise and the mixture stirred under reflux for 2 hours. To the reaction was then added a pre-stirred solution of trimethylaluminium (0.34 ml, 0.68 mmol) and 3-phenylpropanimidamide (100 mg, 0.68 mmol, CAS RN 24442-03-3) in THF (1 ml). The ether was taken off under vacuum and then the reaction stirred under reflux for 4 hours. The reaction mixture was poured onto a slurry of silica in DCM. The resulting slurry was stirred for 15 minutes and then concentrated in vacuo. The resulting solid (dry loaded crude product on silica) was then purified by column chromatography ($SiO_2$: 0-10% MeOH in DCM) to yield 2-(2-phenylethyl)-5-(tetrahydro-2H-pyran-2-yloxy)pyrimidin-4(3H)-one (65 mg, 35% yield).

$^1$H NMR (400 MHz, $CD_3OD$): δ 7.70 (br. s., 1H), 6.98-7.37 (m, 5H), 5.45 (br. s., 1H), 3.79-3.96 (m, 1H), 3.58-3.68 (m, 1H), 2.97-3.12 (m, 2H), 2.75-2.95 (m, 2H), 1.13-2.18 (m, 6H).

MS ES$^+$: 301.

1.5.1 Intermediate 37 (Prepared According to Scheme 5 Step (a))

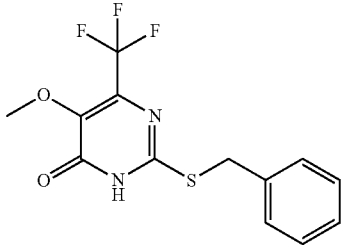 [SMILES: COc1c(C(F)(F)F)nc(SCc2ccccc2)[nH]c1=O]

2-(Benzylsulfanyl)-5-methoxy-6-(trifluoromethyl)-pyrimidin-4(3H)-one

To a solution of diisopropylamine (283 mg, 2.79 mmol) in THF (15 ml) at 0° C. was added n-butyl lithium (1.80 ml, 2.80 mmol). The mixture was stirred for 15 minutes and then cooled to −78° C. before ethyl 2-methoxyacetate (300 mg, 2.54 mmol) was added drop-wise and the whole mixture was allowed to stir for 30 minutes. Ethyl 2,2,2-trifluoroacetate (361 mg, 2.54 mmol) was then added and the reaction mixture was allowed to warm to room temperature and stirred for 2 hours. A solution of benzyl carbamimidothioate (422 mg, 2.54 mmol) in ethanol (15 ml) was then added and the resulting mixture was stirred at reflux for 4 hours and then allowed to cool and stirred at room temperature for 72 hours. The reaction mixture was then evaporated and diluted with DCM and the organic extracts was washed with water. The organic layer was isolated and evaporated and the resulting residue purified by column chromatography (SiO$_2$: 0-10% MeOH in DCM) to yield 2-(benzylsulfanyl)-5-methoxy-6-(trifluoromethyl)pyrimidin-4(3H)-one (319 mg, 40%).

$^1$H NMR (400 MHz, CD$_3$OD): δ 7.43 (m, 2H), 7.10-7.36 (m, 3H), 4.43 (s, 2H), 3.92 (s, 3H).

MS ES$^+$: 317.

2. EXAMPLES

2.1. Example 1 (Prepared According to Scheme 1)

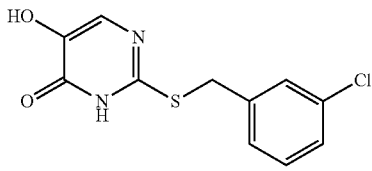 [SMILES: O=c1[nH]c(SCc2cccc(Cl)c2)ncc1O]

2-(3-Chlorobenzylthio)-5-hydroxypyrimidin-4(3H)-one

To a solution of 2-[(3-chlorobenzyl)sulfanyl]-5-(tetrahydro-2H-pyran-2-yloxy)pyrimidin-4(3H)-one (0.60 g, 1.71 mmol) (Intermediate 2) in dioxane (5 ml) was added HCl, 4M in dioxane (0.43 ml, 1.71 mmol). The reaction mixture was stirred at RT overnight before being filtered. The resulting mass was triturated with diethyl ether and then isolated and dried to give a yellow solid. This was recrystallised from methanol (4 ml) and ethyl acetate (15 ml) to yield 2-(3-chlorobenzylthio)-5-hydroxypyrimidin-4(3H)-one (137 mg, 30%).

$^1$H NMR (400 MHz, DMSO-d$_6$): δ 12.50-13.10 (s, br, 1H), 8.90-9.10 (s, br, 1H), 7.25-7.53 (m, 5H) and 4.34 (s, 2H).

MS ES$^+$: 269.

The compounds according to Examples 2 to 14 were prepared in a similar manner to the methodology described for Example 1 and according to Scheme 1 step (c).

2.2. Example 2

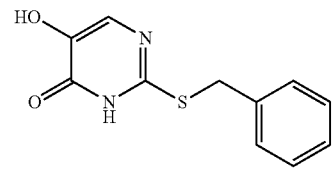

2-(Benzylsulfanyl)-5-hydroxypyrimidin-4(3H)-one

Prepared from 2-(benzylsulfanyl)-5-(tetrahydro-2H-pyran-2-yloxy)pyrimidin-4(3H)-one (Intermediate 4).

Alternatively, to a solution of 2-(benzylsulfanyl)-5-(tetrahydro-2H-pyran-2-yloxy)pyrimidin-4(3H)-one (Intermediate 4) (70 mg, 0.22 mmol) in methanol (1.5 ml) was added PTSA (42 mg, 0.22 mmol). The reaction mixture was stirred at RT overnight before being was evaporated and taken up in DCM. The organics were washed with water, concentrated and purified by column chromatography (SiO$_2$: 0-10% MeOH in DCM) to yield 2-(benzylsulfanyl)-5-hydroxypyrimidin-4(3H)-one.

$^1$H NMR (400 MHz, DMSO-d$_6$): δ 12.35-12.50 (s, br, 1H), 9.10-9.60 (s, br, 1H), 7.21-7.49 (m, 6H) and 4.34 (s, 2H).

MS ES$^+$: 235.

2.3 Example 3

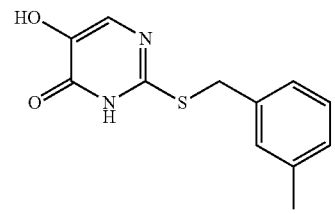 [SMILES: Cc1cccc(CSc2ncc(O)c(=O)[nH]2)c1]

5-Hydroxy-2-[(3-methylbenzyl)sulfanyl]pyrimidin-4(3H)-one

Prepared from 2-[(3-methylbenzyl)sulfanyl]-5-(tetrahydro-2H-pyran-2-yloxy) pyrimidin-4(3H)-one (Intermediate 5).

$^1$H NMR (400 MHz, DMSO-d$_6$): δ 9.27-9.40 (s, br, 1H), 7.39-7.51 (m, 1H), 7.15-7.24 (m, 4H), 7.03-7.10 (m, 1H), 7.32 (s, 2H) and 2.28 (s, 3H).

MS ES$^+$: 249.

2.4 Example 4

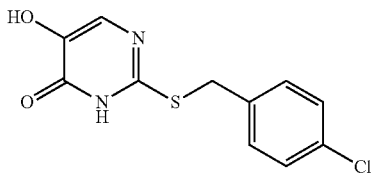 [SMILES: O=c1[nH]c(SCc2ccc(Cl)cc2)ncc1O]

2-[(4-Chlorobenzyl)sulfanyl]-5-hydroxypyrimidin-4(3H)-one

Prepared from 2-[(4-chlorobenzyl)sulfanyl]-5-(tetrahydro-2H-pyran-2-yloxy)pyrimidin-4(3H)-one (Intermediate 3).
$^1$H NMR (400 MHz, DMSO-$d_6$) δ 7.28-7.56 (m, 5H) and 4.33 (s, 2H).
MS ES$^+$: 269.

2.5 Example 5

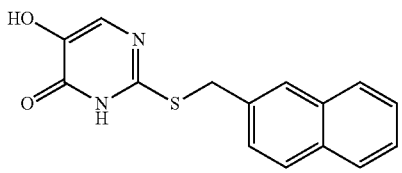 [SMILES: O=c1[nH]c(SCc2ccc3ccccc3c2)ncc1O]

5-Hydroxy-2-[(naphthalen-2-ylmethyl)sulfanyl]pyrimidin-4(3H)-one

Prepared from 2-[(naphthalen-2-ylmethyl)sulfanyl]-5-(tetrahydro-2H-pyran-2-yloxy)pyrimidin-4(3H)-one (Intermediate 6).
$^1$H NMR (400 MHz, MeOD-$d_4$): δ 7.80-7.97 (m, 4H), 7.45-7.58 (m, 4H) and 4.61 (s, 2H).
MS ES$^+$: 285.

2.6 Example 6

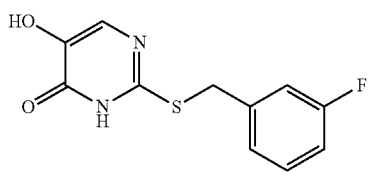 [SMILES: O=c1[nH]c(SCc2cccc(F)c2)ncc1O]

2-[(3-Fluorobenzyl)sulfanyl]-5-hydroxypyrimidin-4(3H)-one

Prepared from 2-[(3-fluorobenzyl)sulfanyl]-5-(tetrahydro-2H-pyran-2-yloxy)pyrimidin-4(3H)-one. (Intermediate 7).
$^1$H NMR (400 MHz, DMSO-$d_6$): δ 12.80-13.00 (s, br, 1H), 9.25-9.40 (s, br, 1H), 7.32-7.48 (m, 2H), 7.20-7.25 (m, 2H), 7.04-7.12 (m, 1H) and 4.36 (s, 2H).
MS ES$^+$: 253.

2.7 Example 7

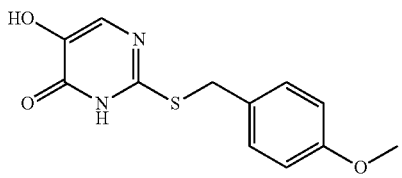 [SMILES: COc1ccc(CSc2ncc(O)c(=O)[nH]2)cc1]

5-Hydroxy-2-[(4-methoxybenzyl)sulfanyl]pyrimidin-4(3H)-one

Prepared from 2-[(4-methoxybenzyl)sulfanyl]-5-(tetrahydro-2H-pyran-2-yloxy)pyrimidin-4(3H)-one. (Intermediate 8).
$^1$H NMR (400 MHz, MeOD-$d_4$): δ 7.48 (s, 1H), 7.28-7.36 (m, 2H), 6.85-6.91 (m, 2H), 4.35 (s, 2H) and 3.79 (s, 3H).
MS ES$^+$: 264.

2.8 Example 8

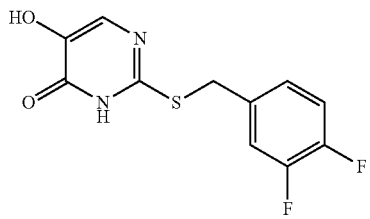 [SMILES: O=c1[nH]c(SCc2ccc(F)c(F)c2)ncc1O]

2-[(3,4-Difluorobenzyl)sulfanyl]-5-hydroxypyrimidin-4(3H)-one

Prepared from 2-[(3,4-difluorobenzyl)sulfanyl]-5-(tetrahydro-2H-pyran-2-yloxy)pyrimidin-4(3H)-one (Intermediate 9).
$^1$H NMR (400 MHz, MeOD-$d_4$): δ 7.46 (s, 1H), 7.32-7.40 (m, 1H), 7.15-7.25 (m, 2H) and 4.41 (s, 2H).
MS ES$^+$: 271.

2.9 Example 9

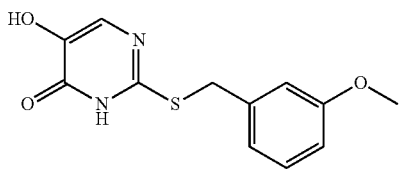 [SMILES: COc1cccc(CSc2ncc(O)c(=O)[nH]2)c1]

5-Hydroxy-2-[(3-methoxybenzyl)sulfanyl]pyrimidin-4(3H)-one

Prepared from 2-[(3-methoxybenzyl)sulfanyl]-5-(tetrahydro-2H-pyran-2-yloxy)pyrimidin-4(3H)-one. (Intermediate 10).

$^1$H NMR (400 MHz, MeOD-d$_4$): δ 7.48 (s, 1H), 7.19-7.26 (m, 1H), 6.95-7.05 (m, 2H), 6.80-6.88 (m, 1H), 4.40 (s, 2H) and 3.33 (s, 3H).
MS ES$^+$: 265.

2.10 Example 10

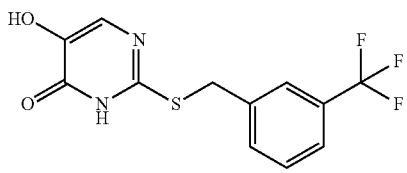 [SMILES: O=c1[nH]c(SCc2cccc(C(F)(F)F)c2)ncc1O]

5-Hydroxy-2-{[3-(trifluoromethyl)benzyl]sulfanyl}pyrimidin-4(3H)-one

Prepared from 5-(tetrahydro-2H-pyran-2-yloxy)-2-{[3-(trifluoromethyl)benzyl]sulfanyl}pyridin-4(3H)-one (Intermediate 11).
$^1$H NMR (400 MHz, MeOD-d$_4$): δ 7.75-7.85 (m, 2H), 7.44-7.60 (m, 3H) and 4.48 (s, 2H).
MS ES$^+$: 303.

2.11 Example 11

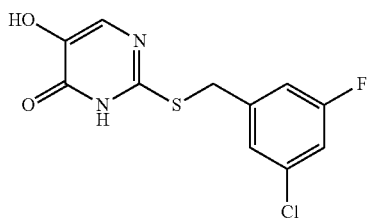 [SMILES: O=c1[nH]c(SCc2cc(F)cc(Cl)c2)ncc1O]

2-[(3-Chloro-5-fluorobenzyl)sulfanyl]-5-hydroxypyrimidin-4(3H)-one

Prepared from 2-[(3-chloro-5-fluorobenzyl)sulfanyl]-5-(tetrahydro-2H-pyran-2-yloxy)pyrimidin-4(3H)-one (Intermediate 12).
$^1$H NMR (400 MHz, MeOD-d$_4$): δ 7.48 (s, 1H), 7.29 (s, 1H), 7.05-7.20 (m, 2H) and 4.42 (s, 2H).
MS ES$^+$: 287.

2.12 Example 12

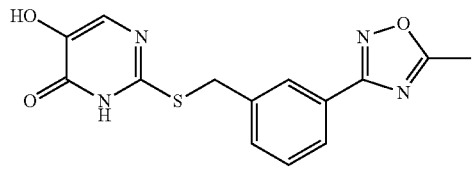 [SMILES: Cc1nc(-c2cccc(CSc3ncc(O)c(=O)[nH]3)c2)no1]

5-Hydroxy-2-{[3-(5-methyl-1,2,4-oxadiazol-3-yl)benzyl]-sulfanyl}-pyrimidin-4(3H)-one Prepared from 2-{[3-(5-methyl-1,2,4-oxadiazol-3-yl)benzyl]sulfanyl}-5-(tetrahydro-2H-pyran-2-yloxy)pyrimidin-4(3H)-one (Intermediate 13).
$^1$H NMR (400 MHz, MeOD-d$_4$): δ 8.13 (s, 1H), 7.92-7.97 (m, 1H), 7.56-7.63 (m, 1H), 7.45-7.52 (s, 2H), 4.48 (s, 2H) and 2.68 (s, 3H).
MS ES$^+$: 317.

2.13 Example 13

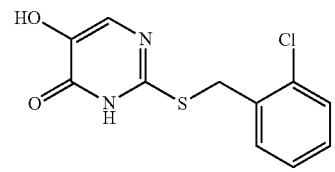 [SMILES: O=c1[nH]c(SCc2ccccc2Cl)ncc1O]

2-[(2-Chlorobenzyl)sulfanyl]-5-hydroxypyrimidin-4(3H)-one

Prepared from 2-[(2-chlorobenzyl)sulfanyl]-5-(tetrahydro-2H-pyran-2-yloxy)pyrimidin-4(3H)-one (Intermediate 14).
$^1$H NMR (400 MHz, DMSO-d$_6$): δ 9.10-9.60 (s, br, 1H), 7.53-7.60 (m, 1H), 7.48-7.57 (s, 2H), 7.27-7.37 (m, 2H) and 4.41 (s, 2H).
MS ES$^+$: 269.

2.14 Example 14

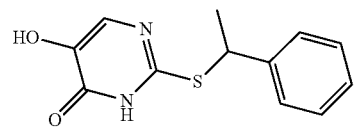 [SMILES: CC(Sc1ncc(O)c(=O)[nH]1)c1ccccc1]

5-Hydroxy-2-[(1-phenylethyl)sulfanyl]pyrimidin-4(3H)-one

Prepared from 2-[(1-phenylethyl)sulfanyl]-5-(tetrahydro-2H-pyran-2-yloxy)pyrimidin-4(3H)-one (Intermediate 15).
$^1$H NMR (400 MHz, DMSO-d$_6$): δ 7.38-7.41 (m, 3H), 7.28-7.34 (s, 2H), 7.23-7.27 (m, 1H), 4.92-4.98 (m, 1H), 1.68 (s, 3H).
MS ES$^+$: 249.

2.15 Example 15 (Prepared According to Scheme 3)

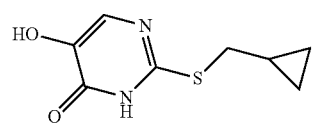 [SMILES: O=c1[nH]c(SCC2CC2)ncc1O]

2-(Cyclopropylmethylthio)-5-hydroxypyrimidin-4(3H)-one

2-[(Cyclopropylmethyl)sulfanyl]-5-(tetrahydro-2H-pyran-2-yloxy)pyrimidin-4(3H)-one (Intermediate 17) (520 mg, 1.84 mmol) was dissolved in dioxane (5 ml) and HCl (0.9 ml, 3.70 mmol) 4M in dioxane was added. A white precipitate formed. The resulting mixture was stirred for 1 hour at RT before pouring into ether and filtering. The solid obtained was dissolved in boiling ethanol, filtered hot, and then water was added drop-wise to the refluxing solution. The ethanol was boiled off until an aliquot withdrawn into a small sample vial showed crystallisation on cooling. The solution was allowed to cool with stirring to RT. The crystals formed were filtered off washed with water and dried to yield 2-(cyclopropylmethylthio)-5-hydroxypyrimidin-4(3H)-one (342 mg, 94%)

$^1$H NMR (400 MHz, DMSO-$d_6$): δ 8.60-9.30 (s, br, 1H), 7.40 (s, 1H), 3.01-3.04 (m, 2H), 1.04-1.18 (m, 1H), 0.52-0.56 (m, 2H) and 0.26-0.29 (m, 2H).

MS ES$^+$: 199.

The compounds according to Examples 16 to 29 were prepared in a similar manner to the methodology described for Example 15 and according to Scheme 3 step (c).

2.16 Example 16

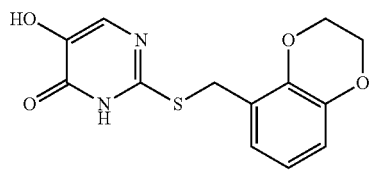 [SMILES: O=c1[nH]c(SCc2cccc3c2OCCO3)ncc1O]

2-[(2,3-Dihydro-1,4-benzodioxin-5-ylmethyl)sulfanyl]-5-hydroxypyrimidin-4(3H)-one Prepared from 2-[(2,3-dihydro-1,4-benzodioxin-5-ylmethyl)sulfanyl]-5-(tetrahydro-2H-pyran-2-yloxy)pyrimidin-4(3H)-one (Intermediate 18).

$^1$H NMR (400 MHz, DMSO-$d_6$): δ 9.25-9.35 (s, br, 1H), 7.40-7.45 (m, 1H), 6.88-6.92 (m, 1H), 6.74-6.81 (m, 2H) and 4.21-4.35 (m, 6H).

MS ES$^+$: 293.

2.17 Example 17

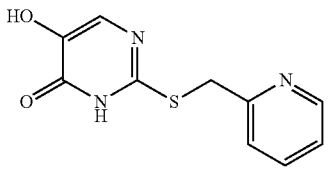 [SMILES: O=c1[nH]c(SCc2ccccn2)ncc1O]

5-Hydroxy-2-(pyridin-2-ylmethylthio)pyrimidin-4(3H)-one

Prepared from 2-(pyridin-2-ylmethylthio)-5-(tetrahydro-2H-pyran-2-yloxy)pyrimidin-4(3H)-one (Intermediate 19).

$^1$H NMR (400 MHz, DMSO-$d_6$) δ 8.73-8.79 (m, 1H), 8.29-8.35 (m, 1H), 7.91-7.95 (m, 1H), 7.75-7.80 (m, 1H), 7.42 (s, 1H) and 4.65 (s, 2H).

MS ES$^+$: 236.

2.18 Example 18

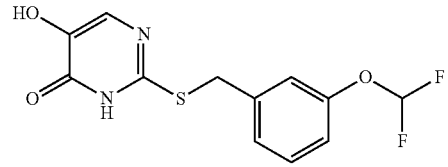 [SMILES: O=c1[nH]c(SCc2cccc(OC(F)F)c2)ncc1O]

2-(3-(Difluoromethoxy)benzylthio)-5-hydroxypyrimidin-4(3H)-one

Prepared from 2-(3-(difluoromethoxy)benzylthio)-5-(tetrahydro-2H-pyran-2-yloxy)pyrimidin-4(3H)-one (Intermediate 20).

$^1$H NMR (400 MHz, DMSO-$d_6$) δ 12.70-13.00 (s, br, 1H), 9.25-9.50 (s, br, 1H), 7.37-7.48 (m, 2H), 7.20-7.28 (m, 2H), 7.01-7.08 (m, 1H) and 4.38 (s, 2H).

MS ES$^+$: 301.

2.19 Example 19

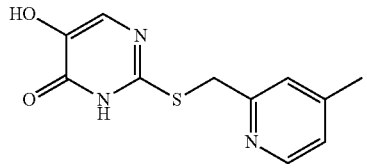 [SMILES: Cc1ccnc(CSc2ncc(O)c(=O)[nH]2)c1]

5-Hydroxy-2-((4-methylpyridin-2-yl)methylthio)pyrimidin-4(3H)-one

Prepared from 2-((4-methylpyridin-2-yl)methylthio)-5-(tetrahydro-2H-pyran-2-yloxy)pyrimidin-4(3H)-one (Intermediate 21).

$^1$H NMR (400 MHz, DMSO-$d_6$) δ 8.69-8.73 (m, 1H), 7.92-7.95 (m, 1H), 7.72-7.78 (m, 1H), 7.43 (s, 1H), 4.63 (m, 2H) and 2.54 (s, 3H).

MS ES$^+$: 250.

2.20 Example 20

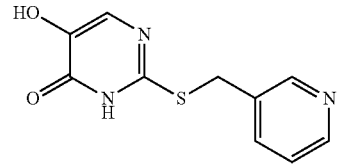 [SMILES: O=c1[nH]c(SCc2cccnc2)ncc1O]

5-Hydroxy-2-(pyridin-3-ylmethylthio)pyrimidin-4(3H)-one

Prepared from 2-(pyridin-3-ylmethylthio)-5-(tetrahydro-2H-pyran-2-yloxy)pyrimidin-4(3H)-one (Intermediate 22).
$^1$H NMR (400 MHz, DMSO-d$_6$) δ 8.65 (s, 1H), 8.39-8.42 (m, 1H), 7.72-7.78 (m, 1H), 7.23-7.36 (m, 1H), 7.16 (s, 1H) and 4.21 (m, 2H).
MS ES$^+$: 236.

2.21 Example 21

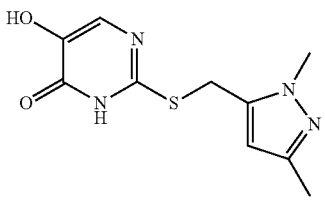 [SMILES: Cc1cc(CSc2ncc(O)c(=O)[nH]2)n(C)n1]

2-((1,3-Dimethyl-1H-pyrazol-5-yl)methylthio)-5-hydroxypyrimidin-4(3H)-one

Prepared from 2-((1,3-dimethyl-1H-pyrazol-5-yl)methylthio)-5-(tetrahydro-2H-pyran-2-yloxy)pyrimidin-4(3H)-one (Intermediate 23).
$^1$H NMR (400 MHz, DMSO-d$_6$) δ 8.88-9.50 (s, br, 1H), 7.45 (s, 1H), 5.95 (s, 1H), 4.34 (s, 2H), 3.73 (s, 3H) and 2.08 (s, 3H).
MS ES$^+$: 253.

2.22 Example 22

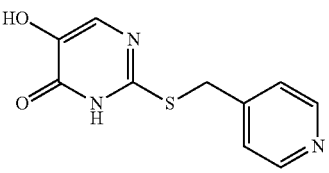 [SMILES: O=c1[nH]c(SCc2ccncc2)ncc1O]

5-Hydroxy-2-(pyridin-4-ylmethylthio)pyrimidin-4(3H)-one

Prepared from 2-(pyridin-4-ylmethylthio)-5-(tetrahydro-2H-pyran-2-yloxy)pyrimidin-4(3H)-one (Intermediate 24).
$^1$H NMR (400 MHz, DMSO-d$_6$) δ 9.34-9.52 (s, br, 1H), 8.60-8.66 (m, 2H), 7.63-7.69 (m, 2H), 7.42 (s, 1H) and 4.44 (s, 2H).
MS ES$^+$: 236.

2.23 Example 23

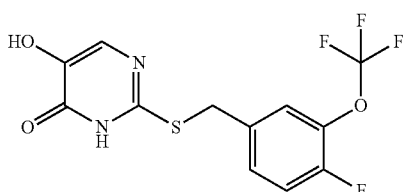

2-(4-Fluoro-3-(trifluoromethoxy)benzylthio)-5-hydroxypyrimidin-4(3H)-one

Prepared from 2-(4-fluoro-3-(trifluoromethoxy)benzylthio)-5-(tetrahydro-2H-pyran-2-yloxy)pyrimidin-4(3H)-one (Intermediate 25).
$^1$H NMR (400 MHz, DMSO-d$_6$) δ 12.75-12.90 (s, br, 1H), 9.31-9.42 (s, br, 1H), 7.60-7.66 (m, 1H), 7.37-7.55 (m, 3H) and 4.44 (s, 2H).
MS ES$^+$: 337.

2.24 Example 24

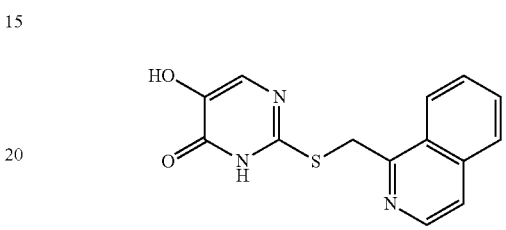

5-Hydroxy-2-[(isoquinolin-1-ylmethyl)sulfanyl]pyrimidin-4(3H)-one

Prepared from 2-[(isoquinolin-1-ylmethyl)sulfanyl]-5-(tetrahydro-2H-pyran-2-yloxy)pyrimidin-4(3H)-one (Intermediate 26).
$^1$H NMR (400 MHz, DMSO-d$_6$) δ 8.41-8.47 (m, 1H), 8.29-8.35 (m, 1H), 8.00-8.06 (m, 1H), 7.79-7.85 (m, 2H), 7.70-7.78 (m, 1H), 7.44 (s, 1H) and 5.06 (s, 2H)
MS ES$^+$286.

2.25 Example 25

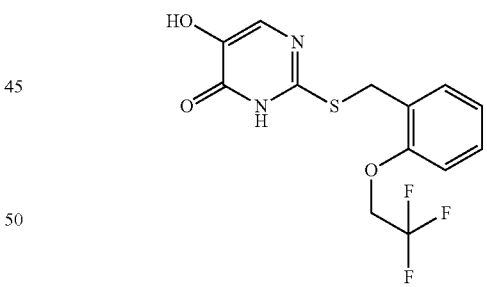

5-Hydroxy-2-{[2-(2,2,2-trifluoroethoxy)benzyl]sulfanyl}-pyrimidin-4(3H)-one

Prepared from 5-(tetrahydro-2H-pyran-2-yloxy)-2-{[2-(2,2,2-trifluoroethoxy)benzyl]sulfanyl}pyrimidin-4(3H)-one. (Intermediate 27).
$^1$H NMR (400 MHz, DMSO-d$_6$) δ 12.60-12.90 (s, br, 1H), 8.95-9.45 (s, br, 1H), 7.38-7.45 (m, 2H), 7.27-7.33 (m, 1H), 7.12-7.17 (m, 1H), 6.95-7.05 (m, 1H), 4.75-4.80 (m, 2H) and 4.30. (s, 2H)
MS ES$^+$333.

2.26 Example 26

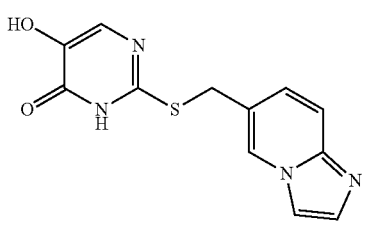 [SMILES: O=c1[nH]c(SCc2ccc3nccn3c2)ncc1O]

5-Hydroxy-2-[(imidazo[1,2-a]pyridin-6-ylmethyl) sulfanyl]-pyrimidin-4(3H)-one

Prepared from 2-[(imidazo[1,2-a]pyridin-6-ylmethyl)sulfanyl]-5-(tetrahydro-2H-pyran-2-yloxy)pyrimidin-4(3H)-one (Intermediate 28).

$^1$H NMR (400 MHz, DMSO-d$_6$) δ 12.70-13.5 (s, br, 1H), 9.35-9.55 (s, br, 1H), 8.70 (s, 1H), 8.12 (s, 1H), 7.83 (s, 1H), 7.64-7.73 (m, 1H), 7.52-7.62 (m, 2H) and 4.47 (s, 2H)

MS ES$^+$275.

2.27 Example 27

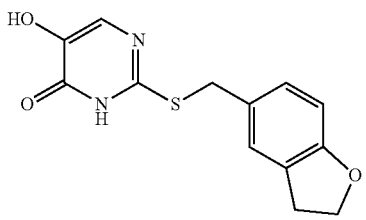 [SMILES: O=c1[nH]c(SCc2ccc3c(c2)CCO3)ncc1O]

2-[(2,3-Dihydro-1-benzofuran-5-ylmethyl)sulfanyl]-5-hydroxypyrimidin-4(3H)-one

Prepared from 2-[(2,3-dihydro-1-benzofuran-5-ylmethyl) sulfanyl]-5-(tetrahydro-2H-pyran-2-yloxy)pyrimidin-4 (3H)-one (Intermediate 29).

$^1$H NMR (400 MHz, DMSO-d$_6$) δ 12.70-12.85 (s, br, 1H), 9.25-9.40 (s, br, 1H), 7.43 (s, 1H), 7.26 (s, 1H), 7.08-7.14 (m, 1H), 7.67-7.76 (m, 1H), 4.45-4.58 (m, 2H), 4.28 (s, 2H) and 3.10-3.18 (m, 2H)

MS ES$^+$299 (M+Na).

2.28 Example 28

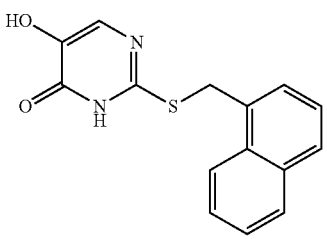 [SMILES: O=c1[nH]c(SCc2cccc3ccccc23)ncc1O]

5-Hydroxy-2-[(naphthalen-1-ylmethyl)sulfanyl]pyrimidin-4(3H)-one

Prepared from 2-[(naphthalen-1-ylmethyl)sulfanyl]-5-(tetrahydro-2H-pyran-2-yloxy)pyrimidin-4(3H)-one (Intermediate 30).

$^1$H NMR (400 MHz, DMSO-d$_6$) δ 12.20-13.25 (s, br, 1H), 8.80-9.60 (s, br, 1H), 8.10-8.18 (m, 1H), 7.97-8.05 (m, 1H), 7.84-7.92 (m, 1H), 7.55-7.71 (m, 3H), 7.45-7.51 (m, 2H) and 4.88 (s, 2H)

MS ES$^+$285.

2.29 Example 29

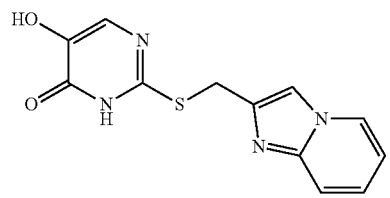 [SMILES: O=c1[nH]c(SCc2cn3ccccc3n2)ncc1O]

5-Hydroxy-2-[(imidazo[1,2-a]pyridin-2-ylmethyl) sulfanyl]-pyrimidin-4(3H)-one

Prepared from 2-[(imidazo[1,2-a]pyridin-2-ylmethyl)sulfanyl]-5-(tetrahydro-2H-pyran-2-yloxy)pyrimidin-4(3H)-one (Intermediate 31).

$^1$H NMR (400 MHz, DMSO-d$_6$) δ 9.11-9.30 (s, br, 1H), 8.48-8.55 (m, 1H), 7.88 (s, 1H), 7.45-7.55 (m, 2H), 7.20-7.28 (m, 1H), 6.83-6.88 (m, 1H) and 4.45 (m, 2H).

MS ES$^+$275.

2.30 Example 30 (Prepared According to Scheme 4 Step (c))

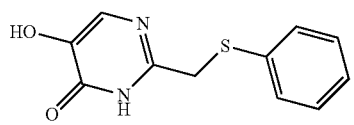 [SMILES: O=c1[nH]c(COc2ccccc2)ncc1O]

5-Hydroxy-2-[(phenylsulfanyl)methyl]pyrimidin-4 (3H)-one

To a solution of 2 2-[(phenylsulfanyl)methyl]-5-(tetrahydro-2H-pyran-2-yloxy)pyrimidin-4(3H)-one (Intermediate 33) (275 mg, 0.86 mmol) in dioxane (4 ml) was added HCl (4M in dioxane; 0.65 ml, 2.59 mmol) and the reaction stirred at RT overnight. The reaction mixture was concentrated under vacuum. The crude residue was purified by column chromatography (SiO$_2$: 0-10% MeOH in DCM) and product fractions concentrated. The resulting solid was purified further by trituration with diethyl ether to yield 5-hydroxy-2-[(phenylsulfanyl)methyl]pyrimidin-4(3H)-one (11 mg, 5% yield).

$^1$H NMR (400 MHz, MeOD-d$_4$): δ 7.38-7.50 (m, 3H), 7.27-7.40 (m, 3H) and 3.98 (s, 2H).

MS ES$^+$: 235.

The compounds according to Examples 31 to 32 were prepared in a similar manner to the methodology described for Example 14 and according to Scheme 4 step (c).

2.31 Example 31

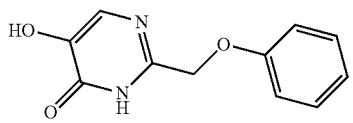

5-Hydroxy-2-(phenoxymethyl)pyrimidin-4(3H)-one

Prepared from 2-(phenoxymethyl)-5-(tetrahydro-2H-pyran-2-yloxy)pyrimidin-4(3H)-one (Intermediate 34).

$^1$H NMR (400 MHz, DMSO-$d_6$): δ 9.30-, 9.80 (s, br, 1H), 9.43-9.47 (m, 2H), 7.25-7.35 (m, 2H), 6.98-7.07 (m, 2H) and 4.86 (s, 2H).

MS ES$^+$: 219.

2.32 Example 32

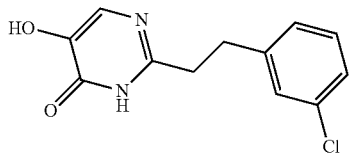 [SMILES: O=c1[nH]c(CCc2cccc(Cl)c2)ncc1O]

2-[2-(3-Chlorophenyl)ethyl]-5-hydroxypyrimidin-4(3H)-one

Prepared from 2-[2-(3-Chlorophenyl)ethyl]-5-(tetrahydro-2H-pyran-2-yloxy)pyrimidin-4(3H)-one (Intermediate 35).

$^1$H NMR (400 MHz, MeOD-$d_4$): δ 7.44 (s, 1H), 7.26-7.46 (m, 2H), 7.15-7.19 (m, 1H), 3.35 (s, 2H, hidden under MeOD peak) and 3.08 (s, 2H).

MS ES$^+$: 251.

2.33 Example 33 (Prepared According to Scheme 4 Step (c))

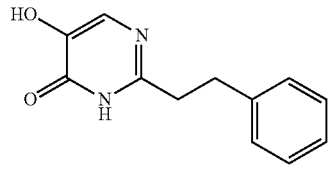 [SMILES: O=c1[nH]c(CCc2ccccc2)ncc1O]

5-Hydroxy-2-(2-phenylethyl)pyrimidin-4(3H)-one

To a solution of 2-(2-phenylethyl)-5-(tetrahydro-2H-pyran-2-yloxy)pyrimidin-4(3H)-one (Intermediate 36) (65 mg, 0.216 mmol) in methyl alcohol (1.5 ml) was added pTSA (41.0 mg, 0.22 mmol). The reaction mixture was stirred at room temperature for 3 hours before being concentrated and then purified by column chromatography (SiO$_2$:0-15% MeOH in DCM) to yield a mixture of desired product and sulphonic acid. This crude material was then taken up in dichloromethane and washed with water. The organics were separated and concentrated to yield 5-hydroxy-2-(2-phenylethyl)pyrimidin-4(3H)-one (5.1 mg, 11% yield).

$^1$H NMR (400 MHz, MeOD-$d_4$): δ 7.40-7.48 (m, 1H), 7.15-7.23 (m, 2H), 7.25-7.33 (s, 3H), 2.95-3.08 (m, 2H) and 2.78-2.88 (m, 2H).

MS ES$^+$: 217

2.34 Example 34 (Prepared According to Scheme 5 Step (b))

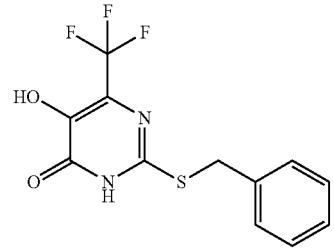 [SMILES: O=c1[nH]c(SCc2ccccc2)nc(C(F)(F)F)c1O]

2-(Benzylsulfanyl)-5-hydroxy-6-(trifluoromethyl)pyrimidin-4(3H)-one

To a solution of 2-(benzylsulfanyl)-5-methoxy-6-(trifluoromethyl)pyrimidin-4(3H)-one (Intermediate 37, 319 mg, 1.00 mmol) in DCM (5 ml) at −78° C. was added boron tribromide (1 M in DCM, 2.00 ml, 2.00 mmol). The reaction mixture was allowed to warm to 0° C. and then stirred for 1 hour. The reaction had not proceeded to completion so it was cooled to −78° C. and a further portion of boron tribromide (1.00 ml, 1.00 mmol) was added. The reaction mixture was then allowed to warm to room temperature and stirred overnight. The whole was then added drop-wise to a solution of aqueous sodium hydroxide solution (2M). The resulting mixture was extracted into dichloromethane and the aqueous layer was acidified to pH 1 with 1M hydrochloric acid and then re-extracted. The combined organics were concentrated in vacuo. The resulting residue was purified by column chromatography (SiO$_2$: 0-10% MeOH in DCM) to yield 2-(benzylsulfanyl)-5-hydroxy-6-(trifluoromethyl)pyrimidin-4(3H)-one (28 mg, 9° 70).

$^1$H NMR (400 MHz, MeOD-$d_4$): δ 7.41-7.46 (m, 2H), 7.23-7.36 (m, 3H) and 4.34 (s, 2H).

MS ES$^+$: 303.

2.35 Example 35

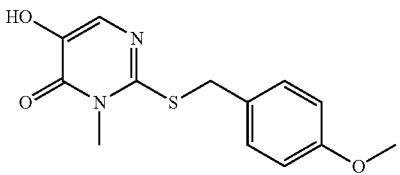 [SMILES: COc1ccc(CSc2ncc(O)c(=O)n2C)cc1]

5-Methoxy-2-(4-methoxybenzylthio)pyrimidin-4(3H)-one

To a solution of 5-hydroxy-2-(4-methoxybenzylthio)pyrimidin-4(3H)-one (Example 7, mg, 0.11 mmol) in DMF (2 ml) at 0° C. was added potassium carbonate (24.0 mg, 0.17 mmol) and then methyl iodide (7 μl, 0.11 mmol). The reaction mixture was allowed to stir at 0° C. for 3 hours, before being quenched with water and extracted with ethyl acetate. The organics were dried (MgSO$_4$) and evaporated to dryness and the resulting residue was purified by column chromatography (SiO$_2$: 0-5% MeOH in DCM). Product fractions were evaporated. The resulting solid was recrystalised from MTBE to yield 5-methoxy-2-(4-methoxybenzylthio)pyrimidin-4(3H)-one (7 mg, 22%).

$^1$H NMR (400 MHz, CD$_2$Cl$_2$): δ 7.48 (s, 1H), 7.21-7.28 (m, 2H), 6.85-6.91 (m, $^2$H), 4.31 (s, 2H), 3.68 (s, 3H) and 3.42 (s, 3H).

MS ES$^+$: 279,

3. BIOLOGICAL EFFICACY OF COMPOUNDS OF THE INVENTION

3.1 In Vitro DAAO Enzyme Assay

The functional activity of compounds inhibiting the DAAO enzyme was determined by utilizing the co-product of the catalysis of D-Serine, H$_2$O$_2$ which can be quantitatively measured using the Amplex Red (Invitrogen) detection. Amplex® Red reagent is a colorless substrate that reacts with hydrogen peroxide (H$_2$O$_2$) with a 1:1 stoichiometry in the presence of hydrogen peroxide to produce highly fluorescent resorufin (excitationemission maxima=570/585 nm). The changes in fluorescence were monitored by a fluorescence plate reader, Envision (Perkin Elmer) and increases in DAAO activity were readily detected upon addition of D-Serine and suppression of this response observed with the application of test compounds.

Human DAAO Enzyme was supplied by the Takeda Pharmaceutical Company (Osaka) and each batch was tested and used at concentrations giving comparable levels of activity. The K$_m$ of D-Serine was measured for each enzyme batch to maintain consistency; this K$_m$ was used in subsequent assays.

On the day of the assay compounds were serially diluted in DMSO before being diluted 1:20 with assay buffer (20 mM Tris ph 7.4). A 5 μl portion of assay buffer was added to the wells of a 384 clear base black walled plate (Corning), 5 μl of diluted compound was then added via automated plate to plate transfer using the Bravo liquid handler (Agilent technologies) followed by 5 μl of human DAAO enzyme and then 5 μl D-Serine 50 mM was added to all but the negative control wells (final concentration of 10 mM). Finally 5 μl Amplex red reagent (Invitrogen) was added to all wells as per manufacturer's protocol. The plate was incubated for 60 minutes in the dark at 25° C. and the fluorescence in each well was measured in the Envision plate reader.

The IC$_{50}$ values for compounds were determined from ten point half log scale dose-response studies and represent the concentration of compound required to prevent 50% inhibition of DAAO activity in the presence of 10 mM D-Serine. Concentration response curves were generated using the average of duplicate wells for each data point and analyzed using nonlinear regression and four parameter curve fit.

3.2 Results

| Example No. | Mean IC$_{50}$ (nM) |
| --- | --- |
| 1 | 120 |
| 2 | 230 |
| 4 | 220 |
| 5 | 120 |
| 6 | 170 |
| 9 | 160 |
| 10 | 150 |
| 11 | 150 |
| 12 | 500 |
| 14 | 1200 |
| 16 | 540 |
| 18 | 190 |
| 20 | 470 |
| 21 | 1600 |
| 26 | 740 |
| 30 | 2800 |
| 31 | 3200 |
| 33 | 1200 |
| 34 | 2700 |
| 35 | 1800 |

These results indicate that compounds of the invention have potent inhibitory activity against the DAAO enzyme. The compounds tested above exhibit IC$_{50}$ values significantly less than 5 μM, with the most potent compounds showing activity at the DAAO enzyme with IC$_{50}$ values <250 nM. Accordingly, the compounds of the invention are expected to have usefulness in the prevention or treatment of conditions; such as those discussed above, in which DAAO enzyme activity is implicated.

The invention claimed is:
1. A compound of formula (1):

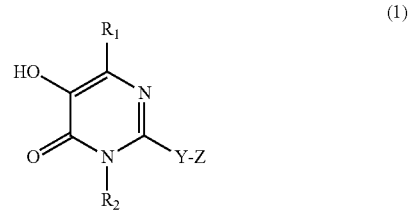

wherein:
R$_1$ is chosen from H, halogen, C$_{1-6}$ alkyl, haloC$_{1-6}$ alkyl, and C$_{1-6}$ alkoxy;
R$_2$ is chosen from H and C$_{1-6}$ alkyl;
Y is chosen from $^a$-A$_1$-S(O)$_p$-A$_2$-, $^a$-A$_1$-C(O)-A$_2$-, and $^a$-A$_5$-O-A$_6$-, wherein $^a$ indicates the point of attachment to the pyrimidinyl ring;
p is chosen from 0, 1, and 2;
A$_1$ is a covalent bond and A$_2$ is C$_{1-3}$ alkylene unsubstituted or substituted with at least one R$_8$, wherein each R$_8$ may be the same or different;
A$_5$ is a covalent bond; A$_6$ is C$_{1-3}$ alkylene unsubstituted or substituted with at least one R$_8$, wherein each R$_8$ may be the same or different;
R$_8$ represents C$_{1-6}$ alkyl;
Z is chosen from aryl, heteroaryl, C$_{3-8}$ cycloalkyl, and heterocyclyl; wherein the aryl, heteroaryl, C$_{3-8}$ cycloalkyl and heterocyclyl groups are unsubstituted or substituted by at least one R$_{10}$; wherein each R$_{10}$ may be the same or different;

$R_{10}$ is chosen from -halogen, —$C_{1-6}$ alkyl, -halo$C_{1-6}$ alkyl, —$C_{0-6}$alkylCN, —$NO_2$, —$C_{0-6}$ alkyl-$CO_2R_{11}$, —$C_{0-6}$ alkyl-$COR_{11}$, —$C_{0-6}$ alkyl-$NR_{11}R_{14}$, —$C_{0-6}$ alkyl-$CONR_{11}R_{12}$, —$C_{0-6}$ alkyl-$NR_{11}COR_{12}$, —$C_{0-6}$ alkyl-$NR_{11}SO_2R_{12}$, —$C_{0-6}$alkyl-$SO_2NR_{11}R_{12}$, —$C_{0-6}$ alkyl-$OCONR_{11}R_{12}$, —$C_{0-6}$ alkyl-$NR_{11}CO_2R_{12}$, —$C_{0-6}$ alkyl-$NR_{11}CONR_{11}R_{12}$, —$C_{0-6}$alkyl-$OR_{13}$, —$C_{0-6}$ alkyl-$SR_{14}$, —$C_{0-6}$alkyl-$SOR_{14}$, —$C_{0-6}$alkyl-$SO_2R_{14}$, —$C_{0-6}$alkyl-$OSO_2R_{14}$, —$C_{0-6}$alkyl-$C_{3-6}$cycloalkyl, —$C_{0-6}$alkyl-aryl, —$C_{0-6}$alkyl-heteroaryl, and —$C_{0-6}$ alkyl-heterocyclyl, wherein the $C_{1-6}$ alkyl, —$C_{0-6}$alkyl-$C_{3-6}$cycloalkyl, —$C_{0-6}$alkyl-aryl, —$C_{0-6}$alkyl-heteroaryl, and —$C_{0-6}$ alkyl-heterocyclyl groups are unsubstituted or substituted with at least one $R_{15}$, wherein each $R_{15}$ may be the same or different;

$R_{11}$ and $R_{12}$ independently are chosen from H and $C_{1-6}$alkyl;

$R_{13}$ is chosen from H, $C_{1-6}$alkyl, $C_{3-6}$ cycloalkyl, —$C_{1-6}$ alkyl-$OR_{18}$, and halo$C_{1-6}$ alkyl;

$R_{14}$ represents $C_{1-6}$alkyl;

$R_{15}$ is chosen from halogen, $C_{1-6}$ alkyl, halo$C_{1-6}$ alkyl, —$C_{0-6}$ alkylCN, —$NO_2$, =O, —$C_{0-6}$ alkyl-$C_{02}R_{16}$, —$C_{0-6}$ alkyl-$COR_{16}$, —$C_{0-6}$ alkyl-$NR_{16}R_{17}$, —$C_{0-6}$ alkyl-$CONR_{16}R_{17}$, —$C_{0-6}$ alkyl-$NR_{16}COR_{17}$, —$C_{0-6}$ alkyl-$NR_{16}SO_2R_{17}$, —$C_{0-6}$ alkyl-$SO_2NR_{16}R_{17}$, —$C_{0-6}$ alkyl-$OCONR_{16}R_{17}$, —$C_{0-6}$ alkyl-$NR_{16}CO_2R_{17}$, —$C_{0-6}$ alkyl-$NR_{16}CONR_{16}R_{17}$, —$C_{0-6}$ alkyl-$OR_{18}$, —$C_{0-6}$ alkyl-$SR_{19}$, —$C_{0-6}$ alkyl-$SOR_{19}$, —$C_{0-6}$ alkyl-$SO_2R_{19}$, and —$C_{0-6}$ alkyl-$OSO_2R_{19}$;

$R_{16}$ and $R_{17}$ independently are chosen from H and $C_{1-7}$ alkyl;

$R_{18}$ is chosen from H, $C_{1-6}$ alkyl, and -halo$C_{1-6}$ alkyl; and $R_{19}$ represents $C_{1-6}$alkyl;

or a pharmaceutically acceptable salt thereof.

2. The compound according to claim 1, wherein $R_1$ represents a hydrogen atom.

3. The compound according to claim 1, wherein $R_2$ represents a hydrogen atom.

4. The compound according to claim 1, wherein Y is chosen from $^a$-$A_1$-S(O)$_p$-$A_2$- and $^a$-$A_5$-O-$A_6$-.

5. The compound according to claim 1, wherein Y is chosen from $^a$—S—$CH_2$— and $^a$—S—CH($CH_3$)—.

6. The compound according to claim 1, wherein Z is chosen from aryl, heteroaryl, and $C_{3-8}$ cycloalkyl, wherein the aryl, heteroaryl and $C_{3-8}$ cycloalkyl groups are unsubstituted or substituted with at least one $R_{10}$.

7. The compound according to claim 1, wherein Z is chosen from phenyl, naphthalenyl, 2,3-dihydro-1,4-benzodioxin-5-yl, 2,3-dihydro-1-benzofuran-5-yl, pyrazolyl, pyridinyl, isoquinolinyl, imidazopyridinyl and cyclopropyl, each of which may be unsubstituted or substituted with at least one $R_{10}$.

8. The compound according to claim 1, wherein $R_{10}$ is chosen from -halogen, —$C_{1-6}$ alkyl, -halo$C_{1-6}$ alkyl, —$C_{0-6}$ alkyl-$OR_{13}$, and —$C_{0-6}$alkyl-heteroaryl, and wherein the —$C_{1-6}$ alkyl and —$C_{0-6}$alkyl-heteroaryl groups are unsubstituted or substituted with at least one $R_{15}$.

9. The compound according to claim 1, chosen from:
2-(3-chlorobenzylthio)-5-hydroxypyrimidin-4(3H)-one;
2-(benzylsulfanyl)-5-hydroxypyrimidin-4(3H)-one;
5-hydroxy-2-[(3-methylbenzyl)sulfanyl]pyrimidin-4(3H)-one;
2-[(4-chlorobenzyl)sulfanyl]-5-hydroxypyrimidin-4(3H)-one;
5-hydroxy-2-[(naphthalen-2-ylmethyl)sulfanyl]pyrimidin-4(3H)-one;
2-[(3-fluorobenzyl)sulfanyl]-5-hydroxypyrimidin-4(3H)-one;
5-hydroxy-2-[(4-methoxybenzyl)sulfanyl]pyrimidin-4(3H)-one;
2-[(3,4-difluorobenzyl)sulfanyl]-5-hydroxypyrimidin-4(3H)-one;
5-hydroxy-2-[(3-methoxybenzyl)sulfanyl]pyrimidin-4(3H)-one;
5-hydroxy-2-{[3-(trifluoromethyl)benzyl]sulfanyl}pyrimidin-4(3H)-one;
2-[(3-chloro-5-fluorobenzyl)sulfanyl]-5-hydroxypyrimidin-4(3H)-one;
5-hydroxy-2-{[3-(5-methyl-1,2,4-oxadiazol-3-yl)benzyl]-sulfanyl}-pyrimidin-4(3H)-one;
2-[(2-chlorobenzyl)sulfanyl]-5-hydroxypyrimidin-4(3H)-one;
5-hydroxy-2-[(1-phenylethyl)sulfanyl]pyrimidin-4(3H)-one;
2-(cyclopropylmethylthio)-5-hydroxypyrimidin-4(3H)-one;
2-[(2,3-dihydro-1,4-benzodioxin-5-ylmethyl)sulfanyl]-5-hydroxypyrimidin-4(3H)-one;
5-hydroxy-2-(pyridin-2-ylmethylthio)pyrimidin-4(3H)-one;
2-(3-(difluoromethoxy)benzylthio)-5-hydroxypyrimidin-4(3H)-one;
5-hydroxy-2-((4-methylpyridin-2-yl)methylthio)pyrimidin-4(3H)-one;
5-hydroxy-2-(pyridin-3-ylmethylthio)pyrimidin-4(3H)-one;
2-((1,3-dimethyl-1H-pyrazol-5-yl)methylthio)-5-hydroxypyrimidin-4(3H)-one;
5-hydroxy-2-(pyridin-4-ylmethylthio)pyrimidin-4(3H)-one;
2-(4-fluoro-3-(trifluoromethoxy)benzylthio)-5-hydroxypyrimidin-4(3H)-one;
5-hydroxy-2-[(isoquinolin-1-ylmethyl)sulfanyl]pyrimidin-4(3H)-one;
5-hydroxy-2-{[2-(2,2,2-trifluoroethoxy)benzyl]sulfanyl}-pyrimidin-4(3H)-one;
5-hydroxy-2-[(imidazo[1,2-a]pyridin-6-ylmethyl)sulfanyl]-pyrimidin-4(3H)-one;
2-[(2,3-dihydro-1-benzofuran-5-ylmethyl)sulfanyl]-5-hydroxypyrimidin-4(3H)-one;
5-hydroxy-2-[(naphthalen-1-ylmethyl)sulfanyl]pyrimidin-4(3H)-one;
5-hydroxy-2-[(imidazo[1,2-a]pyridin-2-ylmethyl)sulfanyl]-pyrimidin-4(3H)-one;
2-(benzylsulfanyl)-5-hydroxy-6-(trifluoromethyl)pyrimidin-4(3H)-one;
5-methoxy-2-(4-methoxybenzylthio)pyrimidin-4(3H)-one;
and a pharmaceutically acceptable salt thereof.

10. The compound according to claim 2, wherein $R_2$ represents a hydrogen atom.

11. The compound according to claim 2, wherein Y is chosen from $^a$-$A_1$-S(O)$_p$-$A_2$- and $^a$-$A_5$-O-$A_6$-.

12. The compound according to claim 3, wherein Y is chosen from $^a$-$A_1$-S(O)$_p$-$A_2$- and $^a$-$A_5$-O-$A_6$-.

* * * * *